United States Patent
Takaki

(10) Patent No.: US 7,531,312 B2
(45) Date of Patent: May 12, 2009

(54) SIMPLIFIED BIOLOGICAL EVALUATION METHOD OF NATURAL AND ARTIFICIAL CHEMICALS BY USING DNA INJURY INDEX AND APPARATUS THEREFOR

(75) Inventor: Atsushi Takaki, Fukuoka (JP)

(73) Assignees: TAS Project Co., Ltd., Fukuoka (JP); Kyushu TLO Company, Limited, Fukuoka (JP)

( * ) Notice: Subject to any disclaimer, the term of this patent is extended or adjusted under 35 U.S.C. 154(b) by 304 days.

(21) Appl. No.: 11/311,360

(22) Filed: Dec. 20, 2005

(65) Prior Publication Data

US 2006/0099634 A1    May 11, 2006

Related U.S. Application Data

(63) Continuation of application No. 10/203,553, filed as application No. PCT/JP01/02095 on Mar. 16, 2001, now abandoned.

(30) Foreign Application Priority Data

Mar. 16, 2000  (JP) ............................... 2000-74200
Mar. 27, 2000  (JP) ............................... 2000-86410

(51) Int. Cl.
*G01N 33/53* (2006.01)
*C12Q 1/68* (2006.01)
*C07H 11/00* (2006.01)

(52) U.S. Cl. ............................. 435/7.1; 435/6; 435/7.2; 422/68.1; 536/4.1

(58) Field of Classification Search .................... 435/6, 435/7.1, 7.2; 422/68.1; 536/4.1
See application file for complete search history.

(56) References Cited

OTHER PUBLICATIONS

Kantha, Sachi Sri et al., "Use of Cu(II)/Ascorbate System in the Screening for Hydroxyl Radical Scavenging Activity in Food Extracts via an ELISA for 8-Hydroxy Deoxyguanosine," American Chemical Society, No. 702, pp. 244-250, (1998).

Kantha, Sachi Sri et al., "A Sensitive Method to Screen for Hydroxyl Radical Scavenging Activity in Natural Food Extracts Using Competitive Inhibition ELISA for 8-Hydroxy Deoxyguanosine," Biotechnology Techniques, vol. 10, No. 12 (Dec. 1996) pp. 933-936.

Toufan Parman et al., "Free Radical Intermediates of Phenytoin and Related Teratogens", Journal of Biological Chemistry, vol. 273, No. 39, pp. 25079-25088 (1998).

*Primary Examiner*—Jezia Riley
(74) *Attorney, Agent, or Firm*—Oliff & Berridge, PLC

(57) ABSTRACT

A biological evaluation method for rational and simply evaluating biological harmfulness or usefulness of a great number of natural and artificial chemicals, foods, etc. This method comprises adding a known amount of 2'-deoxyguanosine (dG) to a solution containing a test substance (drug, pesticide, functional food, etc.), optionally applying UV light and/or adding active oxygen generator, then quantifying 8-hydroxy-2'-deoxyguanosine (8OHdG) in the solution, and evaluating the toxicity or usefulness of the test substance according to the 8OhdG content (a higher 8OhdG content indicates a higher harmfulness of the test substance while a lower 8OhdG content indicates a lower harmfulness or an usefulness thereof). The invention also provide an apparatus for advantageously performing said biological evaluation method and an antioxidant preservative solution to be used in this apparatus.

2 Claims, 5 Drawing Sheets

SIMPLIFIED BIOLOGICAL EVALUATION METHOD OF NATURAL AND ARTIFICIAL CHEMICALS BY USING DNA INJURY INDEX AND APPARATUS THEREFOR

This is a Division of application Ser. No. 10/203,553 filed Aug. 28, 2002, which is a National Stage of Application No. PCT/JP01/02095 filed Mar. 16, 2001. The entire disclosure of the prior application is hereby incorporated by reference herein in its entirety.

TECHNICAL FIELD

The present invention relates to a simplified biological evaluation method of natural and artificial chemicals by using DNA injury index and more particularly to a method for simply evaluating harmfulness or usefulness of natural and artificial chemicals such as pharmaceutical preparations and agricultural chemicals or harmfulness or usefulness of various functional foods and the like by comparing test substance administered group and control group with respect to reaction in which 2'-deoxyguanosine (dG), a constituent of DNA, is converted into 8-hydroxy-2'-deoxyguanosine (8OHdG), an oxidized form, or with respect to a ratio of 8OHdG/dG contained in living organism cell derived products. The present invention further relates to a high sensitive measurement apparatus for DNA oxidation injury index in biological samples.

BACKGROUND ART

Currently, in the environment, there are various types of artificial chemicals, for example, various carcinogenic substances, endocrine disturbing substances and so forth originated from pharmaceutical preparations, agricultural chemicals, detergents, food additives, antiseptics and so forth, that have not existed in the natural environment. Among the natural substances, there are substances on whose toxicity must be taken care because:
1) There is the possibility that deleterious components can exist in natural materials;
2) There is the possibility that in particular when it is formulated in the form of an extract, its biological toxicity is enhanced; and
3) There is the possibility that various components synergistically act to become toxic.

Genetic information is encoded by base pairs of adenine (A), thymine (T), guanine (G) and cytosine (C). The DNA information is injured at a certain frequency due to UV light irradiation, DNA replication error or exposure to various carcinogenic substances or active oxygen species, and ultimately loss, recombination, mutation and so forth of the gene information occurs, thus causing death of cells or the individual or on the contrary triggering naissance of new biological species. The mechanism in which the natural and synthetic chemicals exerts toxicity to animal including humans can be partly explained by such DNA injury.

From this aspect, focusing attention on the oxidation of DNA, 2'-deoxyguanosine (dG) and 2'-deoxyadenosine (dA), which are DNAs (mononucleosides) having purine nuclei bind with hydroxy radicals (.OH), which are active oxygen species, to be oxidized into 8-hydroxy-2'-deoxyguanosine (8OHdG) and 2-hydroxy-2'-deoxyadenosine(2OHdA), respectively. And then the DNA base pairs that should inherently be G:C and A:T are converted to T:A and G:C, respectively. The frequency of occurrence of mistranslation of gene information on the level of DNA is considered to be important information relative to states of various diseases and paid much attention in recent medicinal fields.

Conventionally, biologically acceptable safe concentration of chemicals has been quantified in consideration of
1) Lethal dose when administered to test animals;
2) Amount in which apparent organ disorder such as carcinogenesis or neuropathy occurs when administered to test animals;
3) Amount that influences the fecundity and so forth and by multiplying such minimum effective amount by a safety factor of 100 to 1,000 times.

However, because there are extremely many types of chemicals which are evaluation targets; i.e., as many as at least about 100,000 types, because in the case where biological toxicity is quantified by using mouse or rat, it takes about 2 months for establishing a first generation and a double or more days are necessary for evaluating influence over generations, and because a huge cost is necessary for maintaining the evaluation system and for some other reasons, it has conventionally been practically impossible to evaluate the biological toxicity of all the substances by the conventional method due to restrictions of time and costs.

Many foods currently on the market such as health-care foods and functional foods are in the main those extracted from natural materials or those to which a specific substance is added in the range of safe acceptable amount. However, no objective evaluation system on usefulness (effectiveness) of the foods and the like has been established.

On the other hand, as for a method for measuring 8-hydroxy-2'-deoxyguanosine (8OHdG), which is one of oxidized DNA substances as described above, in biological samples such as leukocytes, parenchyma organ or cell suspension, measurement has been generally performed by extracting nuclear DNA from these cell components and subjecting it to various enzyme treatments, passing it through HPLC (high performance liquid chromatography), and flowing the eluate to an electrochemical detector to measure it in the form of mononucleoside. This method can evaluate oxidation injury of nuclear DNA per se at measurement sensitivity in the order of 10 pg/ml. However, the method involves steps of acid or alkali treatment, enzyme reaction and so forth so that the operation of it is troublesome and secondary DNA oxidation is inevitable due to these treatments so that the method can be practiced only in limited installment.

Likewise, in the case where 8OHdG is measured in urine that contains it in a large amount, a method is used in which after removal of proteins, it is passed through HPLC and an electrochemical detector. However, since urine per se is a biological sample that is very susceptible to oxidation, it has been the most difficult obstacle course how to remove proteins under conditions where oxidation is prevented.

A method for quantifying 8OHdG that is increasingly used recently is an enzyme antibody method (EIA method) by use of monoclonal antibody. Unlike the method by use of HPLC and an electrochemical detector, this method is characterized in that it can detect even when the sample is not in the form of mononucleoside. However, it has defects that it undergoes cross-reaction with other substance than 8OHdG and that it has low detection sensitivity in the order of 1 ng/ml. Accordingly, there have been many problems to be solved in order to generalize it.

On the other hand, it is relatively easy to detect mononucleoside per se in a biological sample since the absolute amount of it in nuclear DNA is relatively large; i.e., about 10,000 to 100,000 times that of oxidized products such as 8OHdG, and due to the characteristics of its chemical structure, UV light absorption measurement apparatus is effectively used in a general detection method. However, pretreatment of analyte to be measured is the same as in the measurement of 8OHdG by use of an electrochemical detector and hence basically the same problems are involved.

It is possible that the artificial chemicals and foods as described above are daily taken by, administered to or brought into contact with humans and therefore it is an urgent necessity to confirm biological toxicity and usefulness, in particular toxicity. However, the present situation is as described above and there are problems in that a long time and high costs are necessary. Accordingly, development of a method for evaluating biological toxicity of artificial chemicals or harmfulness and usefulness of foods in a simplified manner and at low costs has been demanded.

The present invention has been made in response to such a demand and an object of the present invention is to provide a method for evaluating biological harmfulness or usefulness of huge kinds of natural substances and artificial chemicals and foods by in a rational and simplified manner.

Also, an object of the present invention is to provide a measurement apparatus that can accurately quantify in a simplified manner with good reproducibility the amounts of substances that serve as indices in a biological evaluation method, more broadly, oxidized DNA substances, in particular 8-hydroxy-2'-deoxyguanosine (8OHdG), 2-hydroxy-2'-deoxyadenosine (2OHdA) and the like together with the amount of nuclear DNA in the biological sample.

Furthermore, an object of the present invention is to provide an antioxidative preservative solution being able to prevent oxidation injury of DNA in the biological sample in the aforementioned measurement apparatus.

DISCLOSURE OF THE INVENTION

The present inventors have made extensive studies and as a result they have found out that the presence or absence of oxidizing ability or antioxidant ability of a test substance and its degree can be known by adding 2'-deoxyguanosine (dG) to a solution containing a natural or artificial chemical or food which is test substances and measuring after a predetermined time concentration of 8-hydroxy-2'-deoxyguanosine (8OHdG), i.e., oxidized form of 2'-deoxyguanosine in the solution, and that using it as an index biological harmfulness and nontoxicity or usefulness of the test substance can be evaluated. As a result of further study, the present inventors have completed the present invention.

That is, the present invention relates to a biological evaluation method of natural or artificial chemical, comprising the steps of adding a known amount of 2'-deoxyguanosine to a solution containing a specific natural or artificial chemical, quantifying 8-hydroxy-2'-deoxyguanosine in the solution, and evaluating harmfulness or usefulness of the natural or artificial chemical according to the amount of the 8-hydroxy-2'-deoxyguanosine.

In the biological evaluation method for the aforementioned test solution, presence or absence of additive, synergistic or offsetting effect to oxidation injury of gene nucleic acid attributable to the active oxygen in the test solution by adding dG, irradiating UV light and/or adding active oxygen species generator to the solution, and then quantified 8OHdG in the solution.

Therefore, the present invention relates to a biological evaluation method of a natural or artificial chemical, comprising the steps of adding a known amount of 2'-deoxyguanosine to a solution containing a specific natural or artificial chemical, irradiating UV light and/or adding active oxygen species generator to the solution, quantifying 8-hydroxy-2'-deoxyguanosine in the solution, and evaluating harmfulness or usefulness of the natural or artificial chemical according to the amount of the 8-hydroxy-2'-deoxyguanosine by use of, as an index, presence or absence of additive, synergistic or offsetting effect to oxidation injury of gene nucleic acid attributable to the active oxygen of the natural or artificial chemical.

Further, the present invention relates to a biological evaluation method for a food comprising a natural or artificial chemical, comprising the steps of adding a known amount of 2'-deoxyguanosine to a solution containing the food comprising the natural or artificial chemical, quantifying 8-hydroxy-2'-deoxyguanosine in the solution, and evaluating harmfulness or usefulness of the food according to the amount of the 8-hydroxy-2'-deoxyguanosine, and to a biological evaluation method for a food comprising a natural or artificial chemical, comprising the steps of adding a known amount of 2'-deoxyguanosine to a solution containing the food comprising the natural or artificial chemical, irradiating UV light and/or adding active oxygen species generator to the solution, quantifying 8-hydroxy-2'-deoxyguanosine in the solution, and evaluating harmfulness or usefulness of the natural or artificial chemical according to the amount of the 8-hydroxy-2'-deoxyguanosine by use of, as an index, presence or absence of additive, synergistic or offsetting effect to oxidation injury of gene nucleic acid attributable to the active oxygen of the food.

The present invention also relates to a biological evaluation method for a food comprising a natural or artificial chemical, comprising the steps of adding a known amount of 2'-deoxyguanosine to a solution containing the food comprising the natural or artificial chemical and a substance having oxidation injury effect to gene nucleic acid, quantifying 8-hydroxy-2'-deoxyguanosine in the solution, and evaluating usefulness with respect to oxidation injury preventing effect of gene nucleic acid of the food components according to the amount of the 8-hydroxy-2'-deoxyguanosine.

Furthermore, the present invention relates to a biological evaluation method for a test solution, comprising the steps of adding a known amount of 2'-deoxyguanosine to a test solution containing nonspecific chemicals, quantifying 8-hydroxy-2'-deoxyguanosine in the solution, and evaluating antioxidative ability or oxidative ability of the test solution according to the amount of the 8-hydroxy-2'-deoxyguanosine.

The present invention also relates to a biological evaluation method for a chemical or food, comprising the steps of evaluating harmfulness or usefulness of the chemical or food according to ratio between contents of 8-hydroxy-2'-deoxyguanosine and of 2'-deoxyguanosine in a living organism cell derived product collected from an animal including a human, a plant, a bacterium or a fungus administered with a specific chemical or food for a predetermined period.

The present inventors have found out that by perfusion of a biological sample mixed with an antioxidative preservative solution through a dialysis membrane having a cutoff function whose molecular weight is 20 to 50 kD; i.e., a so-called micro dialysis treatment, operation of removal of protein from the biological sample can be performed in an antioxidative environment, and that after the perfusion, by simultaneously subjecting the eluted component from high performance liquid chromatograph to quantification of DNA substance by means of UV light absorption analysis and quantification of DNA oxidation injured product by electrochemical detection to accurately measure the both values under the same conditions, and thereby the state of DNA oxidation injury can be accurately detected.

Therefore, the present invention accomplishes an apparatus for measuring a DNA oxidation injury index, characterized in comprising a) an antioxidative preservative solution to be mixed with a liquid biological sample for cool stocking, the antioxidative preservative solution having to be prepared in an amount 1 to 5 times that of the biological sample;

b) a micro dialysis apparatus for performing micro dialysis treatment by perfusing a perfusion solution comprising an aqueous glycerol solution in a dialysis membrane tube dipped in a mixed solution of the liquid biological sample and the antioxidative preservative solution to prevent a substance having a molecular weight of 20 to 50 kD or more from passing and to make target glycerol concentration of a recovered liquid 10 to 20 wt %;

c) a high performance liquid chromatograph having a column for separating a low molecular weight DNA related substance from the recovered liquid in the micro dialysis treatment;

d) a UV light absorption analyzer for measuring an amount of DNA nucleic acid by performing UV light absorption analysis of an eluate from the column; and e) an electrochemical detector for measuring an amount of DNA oxidation injured product by electrochemically analyzing the eluate from the column; and f) a DNA oxidation injury index of the liquid biological sample is obtained from a ratio between the amount of the measured DNA nucleic acid and the amount of the measured DNA oxidation injured product.

The present invention further relates to an apparatus for measuring a DNA oxidation injury index, characterized in comprising a) a tube for destructing tissue cells for sealing and cool stocking a mixed solution of a biological sample containing cell components and the antioxidative preservative solution in an amount 1 to 5 times that of the biological sample;

b) an apparatus for destructing cells and removing solids for a destructing sample contained in the biological sample in the tube after the sealing/cool stocking to thereby elute free nucleic acid inside and outside the cells in the preservative solution and simultaneously to separate and sediment solids from the destructed sample;

c) a micro dialysis apparatus for performing micro dialysis treatment by perfusing a perfusion solution comprising an aqueous glycerol solution in a dialysis membrane tube dipped in a mixed solution of the liquid biological sample and the antioxidative preservative solution to prevent a substance having a molecular weight of 20 to 50 kD or more form passing and to make a target glycerol concentration of a recovered liquid 10 to 20 wt %;

d) a high performance liquid chromatograph having a column for separating a low molecular weight DNA related substance from the recovered liquid in the micro dialysis treatment;

e) a UV light absorption analyzer for measuring an amount of DNA nucleic acid by performing UV light absorption analysis of an eluate from the column; and f) an electrochemical detector for measuring an amount of DNA oxidation injured product by electrochemically analyzing the eluate from the column; and g) DNA oxidation injury index of the biological sample is obtained from a ratio between the amount of the measured DNA nucleic acid and the amount of the measured DNA oxidation injured product.

Further, the present inventors have found out that as an antioxidative preservative solution for a biological sample in the aforementioned measurement apparatus, an aqueous solution containing 0.5 to 2 mM/l of EDTA, 2 to 5 wt % of methanol, and 10 to 40 wt % of glycerol is particularly useful.

Therefore, the present invention relates to the aforementioned measurement apparatus for the DNA oxidation injury index in which the antioxidative preservative solution is an aqueous solution containing 0.5 to 2 mM/l of EDTA, 2 to 5 wt % of methanol, and 10 to 40 wt % of glycerol, and to an antioxidative preservative solution for a biological sample per se comprising an aqueous solution containing 0.5 to 2 mM/l of EDTA, 2 to 5 wt % of methanol, and 10 to 40 wt % of glycerol.

BEST MODE FOR CARRYING OUT THE INVENTION

Figure 1:
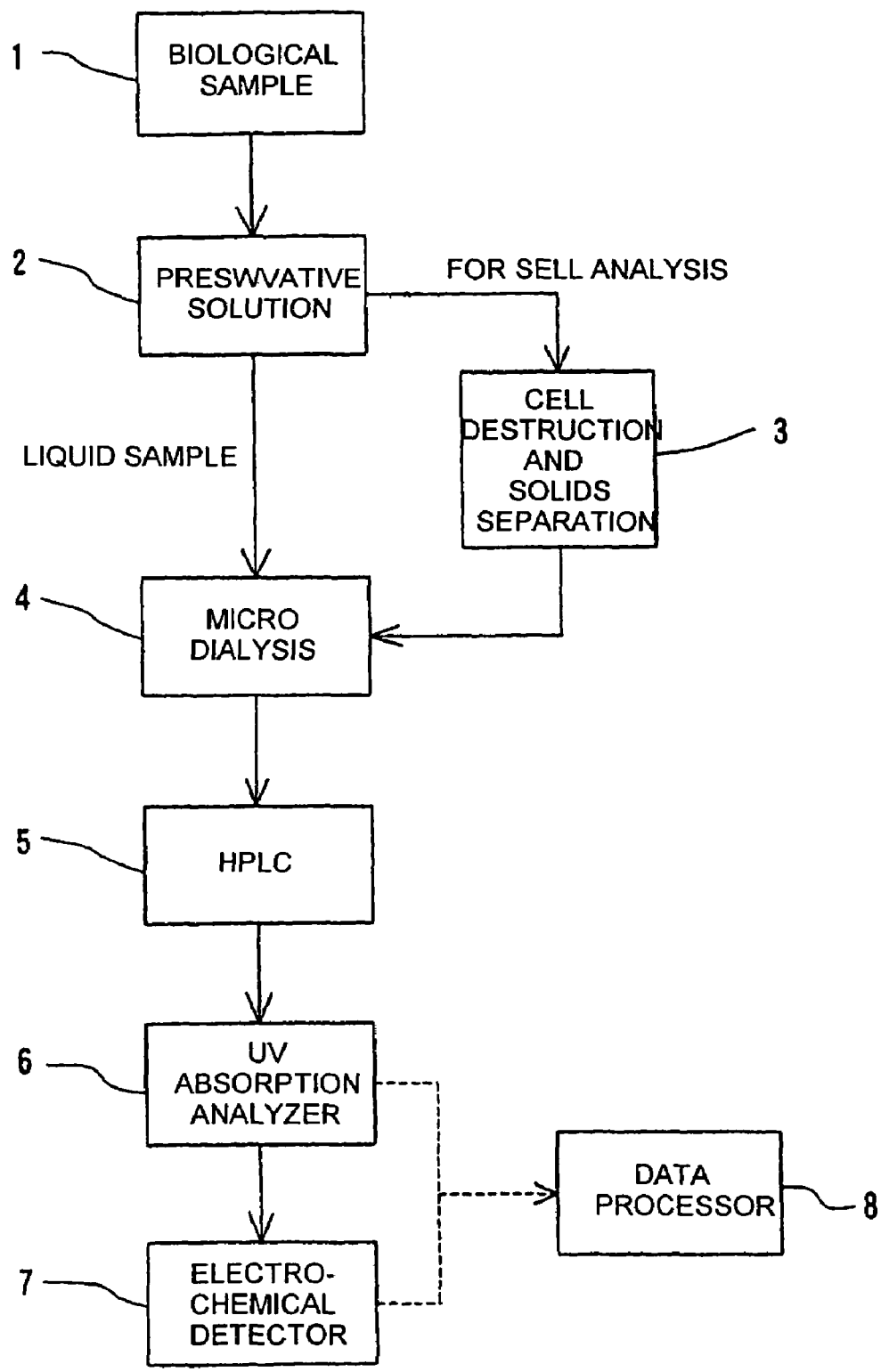
FIG. 1 is a flowchart illustrating the procedure of the biological sample measurement apparatus of the present invention.

In the present invention, "evaluate (presence or absence of) harmfulness or usefulness" means to present a criterion of judgment as to whether or not a test substance has a biological harmfulness (imparting oxidative stress, carcinogenicity, teratogenicity, adverse influence on reproductive potential and so forth), or criterion of judgment as to whether to have harmfulness or usefulness (effectiveness), and degree of the harmfulness or usefulness. "Evaluate antioxidant ability or oxidizing ability" means to present a criterion of judgement as to whether or not a test solution has an antioxidant ability, in other words, whether or not it has a reducing power, or a criterion of judgement as to whether or not a test solution has an oxidizing ability (oxidizing power), and degrees of them.

2'-Deoxyguanosine used in the present invention is a kind of deoxypurine nucleoside, which is a constituent of DNA. Almost all the gene information is encoded by base pairs of adenine (A) and thymine (T), and guanine (G) and cytosine (C). This gene information is injured at a certain frequency by spontaneous mutations (due to UV light irradiation, DNA replication error or the like) or mutations with artificial products (various types of carcinogenic substances, active oxygen and so forth) and ultimately loss, recombination, mutation and so forth of the gene information occurs, thus causing death of cells or the individual or on the contrary triggering naissance of new biological species.

Active oxygen is produced from oxygen incorporated in the body and besides it is produced from natural and artificial chemicals taken into the body that serve as sources or induction factors of an active oxygen and is known to give oxidative injury to proteins, lipids, gene nucleic acids and so forth, which are living organism components. In the case of the dG, it binds with hydroxy radicals (.OH), which is an active oxygen species, to form oxidized 8-hydroxy-2'-deoxyguanosine (8OHdG). The 8OHdG converts original G:C base pair into T:A base pair. That is, the conversion from G:C to T:A means that the gene of individual cell is injured at a certain frequency and the quantity of frequency is naturally considered to give an important index for evaluating self-conservation ability or species conservation ability. In fact, there have been reported that as a typical DNA oxidative injury index 8OHdG has a significant correlation with, for example, ratio of carcinogenesis and occurrence of degenerative diseases of brain ("Experimental Medicine", Vol. 13, No. 15, p. 31-37, 1995), a close relationship with death of cell (apoptosis) ("Modern Medicine", Vol. 51, No. 3, p. 42-47, 1996) and the like.

The present invention further advanced use of 8OHdG as DNA oxidative injury index and tries to evaluate harmfulness and safety of a test substance by presence or absence of ability of the test substance for oxidizing dG to 8OHdG and degree of them. In other words, the present invention uses the ability of the test substance to convert dG into 8OHdG as a criterion of judgment of presence or absence of harmfulness, etc., of the test substance and thus basically differs in technical idea from the conventional system which uses the 8OHdG already present in a biological sample and the like as a scale for the degree of risks of occurrence of cancers or neural degenerative diseases or of senescence. The conversion from dG to 8OHdG in the biological evaluation method of the present invention reflects degree of injury of DNA, which is a design drawing of biological phenomenon and may be said to be a very rational objective index for the evaluation of influences on the self preservation ability or species preservation ability of each individual of organisms including humans.

The test substance on which biological evaluation is to be made by the present invention includes natural and artificial chemicals, for example, pharmaceutical preparations, agricultural chemicals, detergents, food additives, antiseptics, various types of carcinogenic substances, endocrine disturbing substances and in addition air polluting substances, water polluting substance and so forth, as well as foods such as health-care foods or functional foods containing natural and artificial chemicals. The foods include general foods and health-care foods per se and also components thereof. The test substance of the present invention includes aqueous solutions containing unidentified substances (solutions whose composition is unclear, also referred to herein as "test solution"), for example, home waste water, industrial waste water, sewage, city water, purified water, natural water, river water, sea water, lake water, and so forth.

The method of present invention is usually performed by leaving an artificial chemical or food as a test substance or a test solution such as city water together with dG for a predetermined time, and measuring generated 8OHdG. Besides, by further loading an oxidation induction factor to which there is the possibility of exposure in the nature or in vivo, through addition of active oxygen species generator or irradiation with UV light or the like, the interaction of such with the test substance can also be evaluated.

Thus, the method of the present invention can evaluate harmfulness or usefulness of artificial chemicals such as pharmaceutical preparations and agricultural chemicals and natural chemicals or foods in simple and rational manner at low costs. Further, for the chemicals of which indications of approximate allowance and effective amount have been obtained by the method of the present invention and which are of high importance can be further strictly evaluated by the cell cultured evaluation method, in vivo evaluation method as described hereinbelow. The present invention also provides such methods.

Cell Cultured Evaluation Method:

To an animal cell (for example, B9 cell line, which is a mouse lymphocyte cell line), plant cell (for example, tobacco BY-2 cell), or fungi (for example, yeast) in culture medium which contains a test substance is optionally added an oxidant and/or performed irradiation with UV light, and after lapse of a predetermined time, concentrations of dG and 8OHdG derived from the cultured cells are measured and values before and after the treatment are compared. The lower animal and plant cells are, the more adaptability in various environments they have as single units of life themselves (detoxication of artificial chemicals, active oxygen elimination function, etc.). However, usefulness of handling live cells is in that the degree of influence of the test substance on the homeostasis maintaining function that the organisms have can be evaluated thereby. In this sense, a cell evaluation method may be said to be a biomarker (bioindex) which can be used most easily. Cultured cells undergo alternation of generation very quickly so that they can reflect at high sensitivity the frequency of DNA injury that tends to occur at the time of cell fission. In addition, for the quantification of dG and 8OHdG, sufficient measurement can be performed when the cell number of $10^7$ to $10^9$ is available. Therefore, a system that handles a relatively large number of analytes can be constructed by a thermostatic chamber.

In Vivo Evaluation Method:

A test substance is administered to a test animal (for example, mouse) for a predetermined period of time and concentrations of dG and 8OHdG in urine and genital organs (ovary or testis) are measured. Conventionally, biological toxicity of artificial chemicals, etc. has been evaluated from various sides (for example, lifetime, change in body weight, biochemical data of blood, incidence of diseases, etc.). However, it has been nearly impossible to make a comprehensive judgment covering all individual indices. However, DNA injury index represents the quality of design drawing of biological activity and its production amount is considered to be common in all the diseases. In this sense, measurement of production amount of 8OHdG in the present invention is simplest and rational comprehensive index that allows presumption of degree of health in a living organism. The essence of biological activity is concentrated on self-conservation and species conservation, and hence evaluation of reproduction toxicity is of great significance. According to the method of the present invention, target is narrowed down on testis and ovary, which are genital organs of male and female, respectively and fundamental risk of a test substance can also be evaluated based on the degree of injury of design drawing of life of next generation (DNA). Note that, among a series of evaluation methods, the in vivo evaluation method requires the most expense in time and effort and substances whose exposition concentration is high or substances whose exposition concentration is low but has high harmfulness must be finally tested in animals similar to humans (mammalians). However, the present invention is an evaluation method focused only on DNA injury ability, so that time and costs are considerably reduced as compared with the conventional method.

Measurement of 8OHdG concentration in the method of the present invention can be performed, for example, by separating dG and 8OHdG contained in a sample solution by high performance liquid chromatography (HPLC), and by use of a UV light absorption analyzer and an electrochemical detector connected thereto. According to this method, concentrations of dG and 8OHdG can be simultaneously detected. Further, the 8OHdG concentration can also be measured by use of an antibody, preferably a monoclonal antibody that specifically reacts with 8OHdG.

Further, in the case where a biological sample is used, it is preferable that measurement of 8OHdG or the like be performed after efficiently recovering low molecular weight DNA constituents (dG, 8OHdG, etc.) by use of a micro dialysis method (dialysis membrane perfusion method). Concretely, perfusion is conducted by use of a dialysis membrane that can cut off a high molecular weight components of 20 kD to 50 kD. In the case where a biological sample is a liquid sample (plasma, urine, bone marrow, etc.), dialysis is performed by use of a membrane as described above and a mixed solution after the dialysis is subjected to measurement of 8OHdG, etc. In the case of a sample containing cell components (whole blood, cell suspension, tissue, etc.), tissue or cells are destructed by means of a cell crashing apparatus and nucleic acid components that exist in the cytoplasm or nucleus are eluted. Thereafter, solid components are separated by centrifugation and the supernatant liquor is dialyzed by use of a dialysis membrane as described above. dG and 8OHdG in in the recovered dialyzate are measured.

Note that, in the case where a biological sample is used as a test substance, oxidation with active oxygen such as oxidation of dG into 8OHdG starts immediately after the sampling, so that it may be often the case that the state of immediately after the sampling is not accurately reflected to the evaluation results. In such a case, it is preferable that the progress of oxidation after the sampling is prevented by dipping the biological sample in an antioxidative preservative solution mainly comprised a cation chelating agent, an antioxidant and glycerol. The cation chelating agent has an activity of efficiently stopping various biological reactions or enzyme reactions and, for example, sodium ethylenediaminetetraacetate, etc. are used. The antioxidant prevents generation and liberation of hydroxy radicals and, for example, methanol, etc. are used. Also, glycerol has, besides an oxidation preventing effect with a hydroxyl group, a stable activity of preserving a biological sample under the condition of $-20°$ C. to $4°$ C. (conditions under which ordinary biological sample is preserved until time of use) and, for example, 20 to 50% aqueous solution is used. Further, the antioxidative preservative solution is added not only to the biological sample but also to a test substance after dG is added to the test substance and then left to stand for a predetermined time to prevent 8OHdG oxidation until it is measured, thereby enabling measurement of accurate (anti)oxidizing ability after lapse of a predetermined time.

As the aforementioned antioxidative preservative solution, the antioxidative preservative solution comprising an aqueous solution containing 0.5 to 2 mM/l EDTA, 2 to 5 wt % methanol, and 10 to 40 wt % glycerol is preferred. The antioxidative preservative solution specifically prevents induction of 8OHdG from dG (deoxyguanosine) in particular. This is because, firstly EDTA, a cation chelating agent chelates calcium to efficiently stop biological reaction and enzyme reaction, secondly, methanol as an antioxidant prevents production and liberation of hydroxy radicals, and as a third factor, a glycerol solution has an oxidation preventing effect due to an alcohol group (OH group) and at the same time acts as an antifreeze that preserves the analyte in a stable state at $-20°$ C. to $4°$ C. Glycerol also prevents proteolysis and in addition has a preventive effect for enzyme reaction.

In order to confirm usefulness of the aforementioned antioxidative preservative solution, the present inventors:

(1) added 20 μl each of oxidant ($KBrO_3$, 50 mg/ml solution) to 170 μg/l each of various preservative components (candidates) and mixed them;

(2) added 10 μl each of commercially available dG standard solution (2'-deoxyguanosine, 400 μg/l) to the mixed solution to prepare an analyte;

(3) after 30 minutes, mixed 50 μl each of analytes with equal amount (50 μl) of 20% aqueous glycerol solution; and (4) examined oxidation state of each analyte (increase in 8OHdG) by quantifying 8OHdG and dG using the mixed solution as antioxidative preservative solution.

The results are shown in the following table. Note that $KBrO_3$ was adopted as an oxidizing agent because this substance is generally used as food additive such as a bleaching agent for bread and an antiseptic.

| Substance mixed with or diluted to product | Oxidation conditions | 8OHdG $\times 10^{-3}$ | dG | 8OHdG/ dG $\times 10^{-3}$ | Relative initial magnification |
|---|---|---|---|---|---|
| Pure water dilution (immediately after) | — | 0.2710 | 1.0300 | 0.263 | 1 |
| Pure water dilution | $KBrO_3$ 30 minutes | 3.779 | 1.067 | 3.542 | 13.47 |
| #1) EDTA/4Na 1 mM | $KBrO_3$ 30 minutes | 1.098 | 0.997 | 1.101 | 4.19 |
| #2) 10% Gly. | $KBrO_3$ 30 minutes | 1.572 | 1.044 | 1.506 | 5.73 |
| #3) 1% Meth. | $KBrO_3$ 30 minutes | 2.882 | 1.04 | 2.771 | 10.54 |
| #4) 5% Meth. | $KBrO_3$ 30 minutes | 2.359 | 1.054 | 2.238 | 8.51 |
| #5) 10 mg/ml Rafi. | $KBrO_3$ 30 minutes | 3.278 | 1.045 | 3.137 | 11.93 |
| #6) 1 mg/ml Rafi. | $KBrO_3$ 30 minutes | 2.327 | 0.926 | 2.513 | 9.55 |
| #7) 10 mg/ml Glu. | $KBrO_3$ 30 minutes | 2.686 | 1.049 | 2.561 | 9.74 |
| #8) 1 mg/ml Glu. | $KBrO_3$ 30 minutes | 2.515 | 1.029 | 2.444 | 9.29 |
| #9) 10% Gly + 2.5% Meth. | $KBrO_3$ 30 minutes | 1.335 | 1.045 | 1.278 | 4.86 |
| #10) 10% Gly + 2.5% Meth. + 1 mM EDTA/4Na | $KBrO_3$ 30 minutes | 0.978 | 1.058 | 0.924 | 3.51 |
| #11) $KBrO_3$ 10 mg/ml | ($KBrO_3$) 15 minutes | 3.991 | 1.011 | 3.95 | |
| #12) $KBrO_3$ 10 mg/ml | ($KBrO_3$) 60 minutes | 3.677 | 1.014 | 3.63 | |
| #13) $KBrO_3$ 1 mg/ml | ($KBrO_3$) 15 minutes | 0.715 | 0.975 | 0.73 | |
| #14) $KBrO_3$ 1 mg/ml | ($KBrO_3$) 60 minutes | 0.788 | 1.022 | 0.77 | |
| #15) $KBrO_3$ 1 mg/ml | 15 Minutes + 90 minutes in preservative solution | 0.727 | 1.018 | 0.71 | |
| #16) $KBrO_3$ 0.1 mg/ml | ($KBrO_3$) 15 minutes | 0.222 | 1.02 | 0.22 | |
| #17) $KBrO_3$ 0.1 mg/ml | ($KBrO_3$) 60 minutes | 0.183 | 1.025 | 0.18 | |

On the first line of table above, there are described the data in the case of "pure water analyte" obtained by use of pure water instead of the mixed solution obtained in (1) above, and on the second line, there are described the data in the case of "pure water/oxidantanalyte" obtained by use of a mixed solution containing pure water instead of the preservative solution and containing a prescribed amount of oxidant ($KBrO_3$). As will be apparent from the table above, the concentration of dG in pure water analyte is 1.0300 VS (value expressed in terms of output of UV absorption analyzer; in this case, standard concentration of dissolved dG was 10 μg/ml). In the stages of preparation and measurement, the concentration of already existing 8OHdG is 0.2710 mVs (value expressed in terms of output of the electrochemical detector; the output of 5 ng/ml standard 8OHdG corresponded to 7.0 mVs), and 8OHdG/dG ratio was $0.263 \times 10^{-3}$. Then, after 30 minutes in pure water/oxidizing analyte, the 8OHdG concentration was 3.779 mVs and the 8OHdG/dG ratio was $3.542 \times 10^{-3}$, which was 13.47 times that of the case of pure water analyte. Hereinafter, for studying the effects of various preservative components, 8OHdG/dG ratio is used. This is for the purpose of reducing the influence of errors that would be expected to appear in the same tendency in both measured values of 8OHdG and dG, for example, errors on concentration and volume of test solutions on data at each measurement.

Those using EDTA/4Na (concentration upon measurement: 1 mM/l), which is a cation chelating agent as a preservative solution component showed a 8OHdG/dG of $1.101 \times 10^{-3}$, and suppressed at a level of 4.19 times that of the case of ultrapure water analyte under the same oxidative conditions, while those using glycerol (concentration upon measurement: 10 wt %) showed a 8OHdG/dG of $1.506 \times 10^{-3}$, and suppressed at a level of 5.73 times that of the case of pure water analyte under the same oxidative conditions. In the case of those using methanol (concentrations upon measurement: 1 wt % and 5 wt %), which is an antioxidant, they showed 8OHdG/dG ratios of $2.771 \times 10^{-3}$ and $2.238 \times 10^{-3}$, and suppressed at a level of 10.54 times and 8.51 times, respectively, that of the case of ultrapure water analyte under the same oxidative conditions.

The above table shows results of two cases where raffinose and glucose were used in addition to the cases of the aforementioned preservative solution components (EDTA/4Na, glycerol, and methanol) Raffinose is one kind of trisaccharides obtained from sugar beet and, because of its physical and chemical stability, is used as a tissue stabilizing agent added to sperm preservative solution or an organ preservative solution. On the other hand, glucose is the most common monosaccharide and at the same time is known to be a potent antioxidant that exists in largest amounts in vivo (Niki et al., ed.; "Antioxidative Chemicals" Academy Publishing Center, 1994). However, as will be apparent form the above table, 8OHdG/dG ratios in both cases are relatively large about 10 to 12 times as large as that of the case of ultrapure water, so they are unsuitable as antioxidative preservative solution components.

Additional typical substance that exhibits antioxidative property to biological samples includes VC (ascorbic acid) and $NaN_3$ (sodiumazide). However, in spite of extremely strong antioxidative property (reducing property) of VC itself, it conversely serves as a strong oxidant in the presence of a metal cation. In fact, when it was stored for a long period of time as added to a dG solution in such a state that it was brought in contact with air, it was confirmed that a large amount of 8OHdG was induced therefrom. Further, sodium azide is widely used as a preservation solution (stabilizing agent) for components of nucleic acid and various enzymes. This also has strong chemical reactivity and it has been confirmed that it reacts with oxygen in the air or in a sample to derive a large amount of nitrogen oxides.

In contrast, glycerol, methanol, and EDTA are extremely stable chemicals; i.e., they do not induce reproduction of microbes and showed antioxidant ability data overstriding glucose and raffinose as explained above with respect to the above table.

Accordingly, with an expectation of synergistic effect among the aforementioned three elements of which preferable results have been obtained, an antioxidative preservative solution was prepared (No. 10 analyte; a mixture of 10 wt % of glycerol, 2.5 wt % of methanol, and 1 mM/l of EDTA/4Na, concentrations being at the time of measurement). As a result, it was found that those using the antioxidative preservative solution showed an 8OHdG/dG ratio of 0.924 and a magnification for initial value of 3.51 and greatly suppressed the oxidation of dG. Therefore, it is the components of No. 10 analyte (the aforementioned three elements) that are suitable as components of the antioxidative preservative solution. The above blending ratios are within the ranges of suitable component concentrations, respectively, for being supplied to a measurement system starting with liquid chromatograph.

Eventually, the blending ratios of components of the antioxidative preservative solution were set such that concentrations at the time of measurement of respective components that vary by use of a typically 20 wt % aqueous glycerol solution as a perfusion solution in the micro dialysis protein removal treatment can approach the value of No. 10 analyte as described above (provided that the concentration of glycerol at the time of measurement may increase about 10 wt % to about 40 wt % of the analyte, but in consideration of the relationship with the precision of protein removal immediately before the measurement, the upper limitation is about 20 wt %.); i.e., EDTA is set to 0.5 to 2 mM/l, methanol is set to 2 to 5 wt %, and glycerol is set to 10 to 40 wt %.

Further, in the above table, Nos. 11 to 17 analytes are intended to show oxidation state of dG with lapse of time in the case where pure water is used instead of the preservative solution component in the mixed solution to which dG standard solution is added and the concentration of oxidant ($KBrO_3$) is changed in three levels. Nos. 11 and 12 have the same oxidant concentration (10 mg/ml of $KBrO_3$) as the pure water/oxidant analyte at the time of measurement and their 8OHdG concentrations of 3.991 after 15 minutes and of 3.677 after 60 minutes are values close to the 8OHdG concentration of 3.779 of pure water/oxidant analyte (30 minutes). These values are extremely high as compared with about 0.7 to about 0.8 and about 0.2 of Nos. 13 to 17 analytes in which the concentrations of $KBrO_3$ are 1 mg/ml and 0.1 mg/ml, respectively. These indicate well that when the oxidant ($KBrO_3$) is added to dG without concomitant addition of antioxidative preservative solution, oxidation proceeds depending on the addition amount thereof.

These results suggest that 8OHdG is induced from dG depending on the concentration of $KBrO_3$ and since substantially no difference in the induction amount of 8OHdG is observed between after 15 minutes and after 60 minutes, the oxidative reaction with $KBrO_3$ quickly occurs and thereafter reaches a constant level. Therefore, DNA oxidation function of various food additives including daily taken through oral route, for example $KBrO_3$, can be clearly grasped by the measurement apparatus of the present invention and can be used for restudy of acceptable concentrations thereof.

The biological evaluation method of the present invention is practiced, for example, as follows. First, a test substance is diluted in multiple stages to form test solutions, into which a known concentration of 2'-deoxyguanosine (dG) is added and left to stand it from ice temperature to about 50° C., preferably at room temperature for a predetermined time, and then amount of produced 8-hydroxy-2'-deoxyguanosine (8OHdG) is measured (this value is defined as A). Separately, the amount of 8OHdG after an ultrapure water solution of dG is left to stand under the same conditions as above for a predetermined time is measured (this value is defined as B). If A is greater than B, the test substance is evaluated to have oxidation induction ability and conversely if A is smaller than B, the test substance is evaluated to have antioxidant ability. In either case, it is judged that the greater the difference is, the greater degree of oxidation induction ability or antioxidant capability the test substance has.

The generation of active oxygen is a phenomenon inevitable to perform biological activity. However, it has been clarified that if the system for eliminating its physiological activity functions only insufficiently, the DNA oxidation injury increases, resulting in carcinogenesis and lowered induction of cell activity (senescence), which in turn lead to death of cell (apoptosis). By the present invention, evaluation as to how much the toxicity of active oxygen is eliminated by a test substance (whether or not it has effectiveness) on DNA nucleic acid level, single cell level, and individual level, or as to how much the toxicity is increased by the test substance (whether or not it is toxic) can be made in a simple manner.

Further, the effectiveness of foods such as various healthcare foods and functional foods, can in other words, be said to depend on how efficiently the toxicity of active oxygen that is generated in vivo can be eliminated. Therefore, according to the present invention, the antioxidant ability of various foods can be rendered objective using DNA oxidation injury as an index.

UV light directly acts on nuclear DNA and is an important factor for causing DNA oxidation injury. No living organism on the earth can escape from the influence thereof. There is the possibility that synthetic chemicals discharged in natural environment or natural chemicals existing in the nature are also activated (radicalized) by UV light irradiation, and thus, biotoxicity that is generated by uptake of the activated synthetic chemicals or coming into contact with the synthetic chemicals cannot be disregarded either. According to the present invention, additive, synergistic or canceling effect between test substances such as the above-mentioned synthetic chemicals and UV light can also be evaluated simply. In addition, the present invention provides a simple evaluation method for additive, synergistic or canceling effect between an active oxygen generator and test substances. Further, according to the present invention, a known amount of dG is added to a solution containing a chemical that has been confirmed to have gene oxidation injury activity and a test substance, and 8OHdG in the above solution is quantified to evaluate the presence or absence of effectiveness of gene injury preventive activity of the test substance according to the amount thereof. Here, by selecting those having high possibilities to be exposed in daily living as the chemical that has been confirmed to have gene oxidation injury effect, evaluation of a test substance can be made in a state closer to reality. In particular, by selecting food as the test substance, the influence of mixture of food and gene oxidation injurious chemicals can be evaluated.

In the biological evaluation method of the present invention, living organism cell derived products collected from animals including humans, plants, bacteria or fungi that have been administered with chemicals or foods or that have taken up or contacted them, for example, blood, urine, other bodily fluid, tissue destruction fluid or cell destruction fluid and so forth as test subjects, and content ratio of 8OHdG and dG (8OHdG/dG) in the test subject are calculated and the harmfulness or usefulness of the foods or chemicals is evaluated according to the magnitude of the content ratio (a higher content of a chemical or food indicates a higher harmfulness and a lower content of chemical or food indicates a higher usefulness).

In the biological evaluation method of the present invention, a substance that has excellent antioxidant ability; i.e., that can efficiently eliminate active oxygen that has been generated for some causes or others, for example, functional foods containing such as various natural or artificial chemicals or subtances whose compositions are unclear, in particular water can treat, improve, or alleviate various diseases in animals including humans when continuously taken up. The antioxidant ability that such a substance should have is nearly equal to the content ratio of 8OHdG and dG in the case where ultrapure water is used. This can be used as one standard.

The measurement apparatus of the present invention can be operated as described below when applied to a biological liquid sample; i.e., an aqueous solution having dissolved therein a test substance such as whole blood, plasma, serum, urine, cerebrospinal fluid and tissue fluid. First, as pretreatment of a sample, a liquid sample is mixed with the same volume of antioxidant preservative solution and thereafter it is stored until measurement. Immediately before measurement operation starting with microdialysis treatment, the stored analyte is returned to room temperature. The test solution perfused and recovered through micro dialysis treatment is supplied to a high performance liquid chromatograph and an eluate containing a dG peak and an 8OHdG peak is supplied to an 8OHdG/dG simultaneous measurement system where measurement is performed. From measured values, DNA oxidation injury index in a biological sample is finally calculated.

The measurement apparatus of the present invention can be operated as described below when applied to a biological sample containing cell components; i.e., those requiring destruction, such as whole blood, cell suspension, organs and tissues. First, an antioxidant preservative solution is injected in a tube for tissue destruction in an amount of 0.5 to 0.1 ml. As the tube for tissue destruction, a sterile tube that is physically suitable for cell destruction and biochemically insensitive to DNAase or RNAase, for example, "Fast DNA tube" manufactured and sold by Bio101 Corp. in U.S.A. can be used. Then, 100 to 200 mg of a biological cell sample is placed in the tube and immediately ice cooled. When preparations of cell destruction and related operations are ready, tissue is destructed by use of a special-purpose destruction apparatus, for example, "FastPrep FP120" type apparatus manufactured and sold by Bio101 Corp. in U.S.A. and free nucleic acid inside and outside cells are eluted in a preservative solution. Solids are removed by centrifugation from the preservative solution containing the free nucleic acid and the supernatant fluid is defined as a stock analyte. The stock analyte is returned to room temperature immediately before measurement and subjected to micro dialysis treatment. The test solution perfused and recovered through micro dialysis treatment is supplied to high performance liquid chromatograph and its elute containing a dG peak and an 8OHdG peak is supplied to an 8OHdG/dG simultaneous measurement system where measurement is performed. From the measured values, finally DNA oxidation injury index of the biological sample is calculated.

The antioxidant preservative solution is basically a solution of a cation chelating agent and an antioxidant dissolved in a 10 to 40% aqueous glycerol solution. This is stored at a temperature of ice cooling condition or lower and in a light-shielded state until a biological sample is mixed therein. Preferred blending ratios of components are as follows.

| | |
|---|---|
| Glycerol: | 10 to 40 wt % |
| Methanol: | 2 to 5 wt % |
| EDTA/4Na: | 0.5 to 2 mM/l |

In the above blending ratios of components, methanol and EDTA/4Na may be optionally added. Preservation of the prepared preservative solution per se or preservation after mixing with a biological sample can be performed in a light-shielded and sealed state in the following manner.

Short Preservation for about 2 to 3 days:
   In a refrigerator (4° C.).
Medium preservation for about half the year:
   In a refrigerator (−10 to −20° C.).
Long preservation for half the year or more:
   In a refrigerator (−80° C.) after purging the air in the sample tube with nitrogen gas.

In the aforementioned micro dialysis, a dialysis membrane tube having a cut off function of blocking a high molecular weight component of 20 to 50 kD is dipped in an analyte and low molecular weight DNA components are efficiently recovered from the analyte by use of an apparatus including a perfusion system with the tube in which a perfusion solution passes. The recovered components include dG, $C_{10}H_{13}N_5O_4$, MW 267, 8OHdG, $C_{10}H_{13}N_5O_5$, MW 283, etc. The perfusion conditions use basically the following values.

| | |
|---|---|
| Perfusion solution: | 20% Glycerol solution |
| Perfusion temperature: | Room temperature |
| Perfusion rate: | 0.5 to 2 µl/minute |

However, in order to increase the recovery rate, or improve S/N ratio of an objective component, these conditions may be changed as appropriate.

The low molecular weight DNA components recovered by the micro dialysis are sent into a column of high performance liquid chromatograph and eluted from the column by component peak such as 8OHdG, dG, etc. The eluate from the column is first sent to a sample cell in a UV absorption analyzer to measure dG content, and then sent to an electrochemical detector, where 8OHdG content is measured.

The procedure of the measurement apparatus of the present invention as stated above is arranged in accordance with the flowchart in FIG. 1 as follows.

Step 1: Collection of a biological sample
Step 2: Preserved with cooling after mixing the biological sample with a preservative solution
Step 3: Destruction of a sample for cell analysis mixed with a preservative solution in the tube and separation of solids.
Step 4: Micro dialysis treatment of the preserved liquid sample or a sample for cell analysis after destruction and separation.
Step 5: Supply of the sample components perfused and extracted by dialysis to high performance liquid chromatograph (HPLC).
Step 6: Sending the eluate from the chromatograph column to a sample cell of a UV light absorption analyzer to measure dG content.
Step 7: Passing the eluate from the column that has passed the above sample cell to an electrochemical detector to measure 8OHdG content.
Step 8: Processing 8OHdG/dG ratio and other data by use of the measured values in the Steps 6 and 7.

Next, the present invention will be illustrated in more detail by way of examples below. However, the present invention should not be construed as being limited thereto.

EXAMPLE 1

Solutions in various concentrations (0.0005 ppm, 0.005 ppm, 0.05 ppm, 0.5 ppm and 5 ppm) of pentachlorophenol (PCP, herbicide), bisphenol A (BPA, resin raw material), and Resveratol (RVT, one kind of polyphenol) were prepared and 180 µl portions were injected into each well of two 99-well plastic plates. Then, 20 µl of 200 µg/ml dG (dissolved in ultrapure water) was added to each well and one of the plates was left to stand as it was at room temperature for 90 minutes and the other plate was irradiated with UV light (254 nm, 860 µW/cm²) for 90 minutes in a UV light irradiation box. After completion of the standing or irradiation, the solution in each well was mixed with the same amount of 20% glycerol solution and dG and 8OHdG were separated from each other by use of HPLC [column used: CA-50DS (manufactured by AICOM CO.), mobile phase solution: 0.1 M phosphate buffer; 3 to 10% methanol, SOS 90 to 100 mg]. Subsequently, nucleosides in the both were quantified by use of the UV light absorption analyzer connected to the HPLC and the electrochemical detector. For comparison, measurement of dG and 8OHdG was performed on ultrapure water alone that had been treated in the same manner. The results were shown Table 1. Although measurements were performed on both nucleosides, the Table below shows only the concentration (ng/ml) of 8OHdG (in examples hereinafter the same).

TABLE 1

| Test Substance | Concentration (ppm) | 90 Minutes' standing | 90 Minutes' UV irradiation |
|---|---|---|---|
| Ultrapure water | | 0.267 | 0.529 |
| PCP | 5 | 0.340 | 5.730 |
| | 0.5 | 0.282 | 0.396 |
| | 0.05 | 0.285 | 0.431 |
| | 0.005 | 0.236 | 0.451 |
| | 0.0005 | 0.260 | 0.585 |
| BPA | 5 | 0.192 | 7.142 |
| | 0.5 | 0.231 | 1.736 |
| | 0.05 | nd | 0.614 |
| | 0.005 | 0.315 | 0.794 |
| | 0.0005 | nd | 0.689 |
| RVT | 5 | nd | 5.582 |
| | 0.5 | nd | 1.378 |
| | 0.05 | nd | 0.571 |
| | 0.005 | nd | 0.690 |
| | 0.0005 | nd | 1.026 |

(In the Table above, each measured value is an average of two measured values, "nd" means no measurement.)

PCP is an agricultural chemical or a softening agent for leather and safety concentration is reported to be 5 mg/kg. However, from the above results, it can be clearly seen that oxidation injury activity due to UV light is extremely elevated and therefore harmfulness is increased at 5 ppm corresponding to 5 mg/kg.

BPA is a representative endocrine disturbing substance (environmental hormone) and at 0.5 ppm or more, it clearly elevates oxidation injury activity due to UV light so that harmfulness is increased. For reference, BPA concentration at which there is the possibility that exposure will actually occur is shown as follows.

In rivers, lakes and ponds:
   About 0.001 ppm in places where it is rich
Water leaching out from general industrial wastes processing plants:
   Maximum about 20 ppm
PC made dishes (95° C., 30 minutes):
   0.005 to 0.1 ppm
Elution from the coating of can for beverage:
   About 0.1 ppm
Elution from the dental cement:
   About 1 ppm in saliva after the treatment of dental caries
Fish:
   About 0.02 to 0.3 ppm The standard on BPA in Japan is 2.5 ppm or less as eluted portion and 500 ppm or less as material. Acceptable uptake amount is 0.05 mg/kg/day, which is common in every country. The present invention can help reviewing these standards.

RVT is a typical polyphenol and is said to be contained in red wine in an amount of about 2 to 10 ppm and its anti-arteriosclerosis activity, etc. have been reported in recent years. However, the above results show that at 0.5 ppm or more, oxidation injury activity due to UV light clearly increases to increase harmfulness. Thus, the present invention can also simply and rationally verify effectiveness (or harmfulness) of substances that have conventionally been considered effective.

In the above tests, the amount of sample necessary for a single measurement is as small as 10 to 100 μl and a measurement peak can be detected in 5 to 10 minutes from the injection of the sample and continuous measurement is possible at a pace of 15 minutes/sample. Therefore, when the present invention is adopted and one HPLC is operated at a pace of 120 hours per week, measurement can be made at a pace of 480 analytes/week and about 2,000 analytes/month. This means that according to the present invention, toxicity and so forth of test substances can be evaluated at such a high pace that has never been reported thus far.

In Example 1, both dG and 8OHdG were simultaneously measured by use of a UV light absorption analyzer and an electrochemical detector. However, measurement of 8OHdG only may be performed. In such a case, a large amount of sample measurement can be done in a short time at high sensitivity by use of a measurement kit using monoclonal antibody [for example, trade name 8-OHdG Check (manufactured by Nippon Aging Control Laboratory).

EXAMPLE 2

Solutions of predetermined concentrations of vitamin C (VC), vitamin E (VE), catechin (Cate) and tannic acid (Tan) were prepared and 180 μl portions were injected into each well of two 99-well plastic plates. Then, 20 μl of 200 μg/ml dG (dissolved in ultrapure water) was added to each well and one of the plates was left to stand as it was at room temperature for 90 minutes and the other plate was irradiated with UV light (254 nm, 860 μW/cm$^2$) for 90 minutes in a UV light irradiation box. After completion of the standing or irradiation, the solution in each well was mixed with the same amount of 20% glycerol solution and dG and 8OHdG were quantified in the same manner as in Example 1. For comparison, measurement of dG and 8OHdG was performed on distilled water alone that had been treated in the same manner. The results are shown in Table 2.

TABLE 2

| Test Substance | Concentration | 90 Minutes' standing | 90 Minutes' UV irradiation |
|---|---|---|---|
| distilled water | | 0.15 | 1.23 |
| VC | 0.001% | 6.04 | 38.36 |
|  | 0.0001% | 0.63 | 1.51 |
|  | 0.00001% | 0.44 | 0.46 |
| VE | 0.05% | 0.44 | 0.42 |
|  | 0.005% | 0.45 | 0.18 |
|  | 0.0005% | 0.49 | 0.30 |
| Cate | 100 μg/ml | nd | nd |
|  | 10 μg/ml | 133.71 | nd |
|  | 1 μg/ml | 9.07 | nd |
| Tan | 100 μg/ml | 54.00 | 97.07 |
|  | 10 μg/ml | 5.64 | 19.29 |
|  | 1 μg/ml | 0.84 | 1.04 |

(In the Table above, each measured value is an average of two measured values, "nd" means no measurement.)

From the above results, the following conclusion can be obtained.

Although VC is said to be a potent antioxidant, it acts as a very strong oxidation inducing substance for water-soluble dG.

VE is a very stable antioxidant.

Cate induces 8OHdG very strongly regardless of whether or not UV light irradiation was performed. This oxidizing ability is considered to be associated with the bactericidal activity and antiviral activity of Cate. There is high possibility that as in the case of Cate, the 8OHdG inducing ability of a substance can be used as an index (effective concentration index) for bactericidal or bacteriostatic effect or antiviral effect.

Tan exhibits high gene injury inducing effect.

EXAMPLE 3

Solutions of predetermined concentrations of glycerol (Gly) and methanol (Meth) were prepared and 180 μl portions thereof were injected into each well of five 99-well plastic plates. Then, 20 μl of 200 μg/ml dG (dissolved in ultrapure water) was added to each well and one of the plates was left to stand as it was at room temperature for 90 minutes and another plate was left to stand similarly at room temperature for 24 hours. The remaining three plates were irradiated with UV light (254 nm, 860 μW/cm$^2$) for 60 minutes, 90 minutes and 120 minutes, respectively, in a UV light irradiation box. After completion of the standing or irradiation, the solution in each well was mixed with the same amount of 20% glycerol solution and dG and 8OHdG were quantified in the same manner as in Example 1. For comparison, measurement of dG and 8OHdG was performed on ultrapure water alone that had been treated in the same manner. The results are shown in Table 3.

TABLE 3

| Test Substance | Concentration | Standing | | UV irradiation | | |
|---|---|---|---|---|---|---|
| | | 90 minutes | 24 hours | 60 minutes | 90 minutes | 120 minutes |
| Ultrapure water | | 0.323 | 0.382 | 0.231 | 0.382 | 0.645 |
| Gly | 5% | 0.228 | 0.306 | 0.344 | 0.399 | 0.544 |
| | 20% | 0.213 | 0.342 | 1.317 | 1.471 | 1.374 |
| Meth | 5% | 0.146 | 0.336 | 0.181 | 0.209 | 0.332 |
| | 20% | 0.186 | 0.274 | 0.324 | 0.395 | 0.518 |

(In the Table above, each measured value is an average of two measured values. While both Gly and Meth have been reported to have DNA injury preventive effects, the results obtained in this example confirmed their antioxidant ability. In particular, it was confirmed that Gly exhibited antioxidant ability only when left to stand at room temperature while potent antioxidant ability of Meth was confirmed at both the time when left to stand at room temperature and the time when irradiated with UV light.

EXAMPLE 4

Solutions of predetermined concentrations of glucose (Glu), raffinose (Raffi) and sucrose (Suc) were prepared and 180 μl portions thereof were injected into each well of four 99-well plastic plates. Then, 20 μl of 200 μg/ml dG (dissolved in ultrapure water) was added to each well and one of the plates was left to stand as it was at room temperature for 90 minutes. The remaining three plates were irradiated with UV light (254 nm, 860 μW/cm$^2$) for 60 minutes, 90 minutes and 120 minutes, respectively, in a UV light irradiation box. After completion of the standing or irradiation, the solution in each well was mixed with the same amount of 20% glycerol solution and dG and 8OHdG were quantified in the same manner as in Example 1. For comparison, measurement of dG and 8OHdG was performed on ultrapure water alone that had been treated in the same manner. The results are shown in Table 4.

TABLE 4

| Test Substance | Concentration | 90 Minutes' standing | UV irradiation | | |
|---|---|---|---|---|---|
| | | | 60 minutes | 90 minutes | 120 minutes |
| Ultrapure water | | 0.195 | 0.392 | 0.901 | 1.183 |
| Glu | 1 mg/ml | 0.220 | 0.094 | 0.099 | 0.237 |
| | 100 μg/ml | 0.200 | 0.132 | 0.274 | 0.414 |
| | 10 μg/ml | 0.240 | 0.291 | 0.458 | 0.277 |
| | 1 μg/ml | 0.260 | 0.384 | 0.595 | 0.385 |
| | 0.1 μg/ml | 0.295 | 0.399 | 0.702 | 0.410 |
| Raffi | 1 mg/ml | 0.340 | 0.115 | 0.176 | 0.240 |
| | 100 μg/ml | 0.455 | 0.158 | 0.370 | 0.503 |
| | 10 μg/ml | 0.405 | 0.281 | 0.626 | 1.314 |
| | 1 μg/ml | 0.185 | 0.304 | 0.854 | 1.049 |
| | 0.1 μg/ml | 0.205 | 0.375 | 0.689 | 1.127 |
| Suc | 1 mg/ml | 0.300 | 0.127 | 0.309 | 0.364 |
| | 100 μg/ml | 0.280 | nd | 0.379 | 0.648 |
| | 10 μg/ml | 0.235 | 0.333 | 0.690 | 1.279 |
| | 1 μg/ml | 0.185 | 0.358 | 0.708 | 1.143 |
| | 0.1 μg/ml | 0.235 | 0.299 | 0.756 | 1.073 |

(In the Table above, each measured value is an average of two measured values, "nd" means no measurement.)

From the above results, the following conclusion can be obtained.

The potency of antioxidant ability in both cases of standing at room temperature and UV light irradiation can be evaluated as Glu>Raffi≈Suc.

Assuming that normal blood sugar level is about 50 to 100 mg/dl (0.5 to 1 mg/ml), Glu existing in blood can be said to be a very effective antioxidant substance.

Raffi is one kind of natural oligosaccharides and is added to many foods such as soft drinks, health-care drinks and health-care foods, and although its antioxidant ability is not so potent as that of Glu, it is effective at a concentration of 10 μg/ml or more.

Suc exhibits antioxidant ability as potent as that of Raffi.

EXAMPLE 5

Solutions of predetermined concentrations of 1-arginine (Arg), 1-citrulline (Cit) and spermine (Spe), each of which was protamine related substances, were prepared and 180 μl portions thereof were injected into each well of two 99-well plastic plates. Then, 20 μl of 200 μg/ml dG (dissolved in ultrapure water) was added to each well and one of the plates was left to stand as it was at room temperature for 90 minutes and the other plate was irradiated with UV light (254 nm, 860 μW/cm$^2$) for 90 minutes in a UV light irradiation box. After completion of the standing or irradiation, the solution in each well was mixed with the same amount of 20% glycerol solution and dG and 8OHdG were quantified in the same manner as in Example 1. For comparison, measurement of dG and 8OHdG was performed on ultrapure water alone that had been treated in the same manner. The results are shown in Table 5.

TABLE 5

| Test Substance | Concentration | 90 Minutes' standing | 90 Minutes' UV irradiation |
|---|---|---|---|
| Ultrapure water | | 0.219 | 0.422 |
| Arg | 1 mg/ml | 0.173 | 0.299 |
| | 100 μg/ml | 0.150 | 0.305 |
| | 10 μg/ml | 0.153 | 0.253 |
| | 1 μg/ml | 0.186 | 0.323 |
| Cit | 1 mg/ml | 0.156 | 0.125 |
| | 100 μg/ml | 0.120 | 0.225 |
| | 10 μg/ml | 0.179 | 0.305 |
| | 1 μg/ml | 0.184 | 0.332 |
| Spe | 1 mg/ml | 0.179 | 0.112 |
| | 100 μg/ml | 0.154 | 0.351 |
| | 10 μg/ml | 0.150 | 0.328 |
| | 1 μg/ml | 0.140 | 0.297 |

(In the Table above, each measured value is an average of two measured values.)

Protamine is a protein that supports a steric structure of a gene and has an extremely high content of arginine, which is a typical basic amino acid (20 to 70%).

Each of Arg, Cit and Spe exhibited antioxidant ability. In the case of Cit and Spe, their antioxidant ability was particularly high at a high concentration (1 mg/ml).

Although data were not shown, it was confirmed according to the present invention that acidic amino acids generally had a tendency of exhibiting oxidization induction, and basic amino acids had a tendency of preventing oxidation.

EXAMPLE 6

Solutions of various concentrations of uric acid (dissolving fluid: distilled water+0.025% FBS) were prepared and 180 μl portions thereof were injected into each well of two 99-well plastic plates. Then, 20 μl of 200 μg/ml dG (dissolved in ultrapure water) was added to each well and one of the plates was left to stand as it was at room temperature for 90 minutes and the other plate was irradiated with UV light (254 nm, 860 μW/cm$^2$) for 90 minutes in a UV light irradiation box. After completion of the standing or irradiation, the solution in each well was mixed with the same amount of 20% glycerol solution and dG and 8OHdG were quantified in the same manner as in Example 1. For comparison, measurement of dG and 8OHdG was performed on the above dissolving fluid alone that had been treated in the same manner. The results are shown in Table 6.

TABLE 6

| Test Substance | Concentration | 90 Minutes' standing | 90 Minutes' UV irradiation |
|---|---|---|---|
| dissolving fluid | | 0.218 | 1.007 |
| uric acid | 10 µg/ml | 0.147 | 15.619 |
| | 1 µg/ml | 0.175 | 2.369 |
| | 0.1 µg/ml | 0.193 | 0.966 |
| | 0.01 µg/ml | 0.176 | 1.064 |

(In the Table above, each measured value is an average of two measured values.)

Uric acid is said to be a typical in vivo antioxidant. However, as is apparent from the above results, although it can inhibit induction of 8OHdG at an actual in vivo plasma concentration (40 to 80 µg/ml) except for in a strong oxidative environment, it shows a high degree of DNA oxidation injury when UV light was coexistent and its toxicity was increased.

EXAMPLE 7

Solutions of various concentrations of potassium bromate ($KBrO_3$) were prepared and 180 µl portions thereof were injected into each well of two 99-well plastic plates. Then, 20 µl of 200 µg/ml dG (dissolved in ultrapure water) was added to each well and one of the plates was left to stand as it was at room temperature for 15 minutes and the other plate was left to stand for 60 minutes. After completion of the standing, the solution in each well was mixed with the same amount of 20% glycerol solution and dG and 8OHdG were quantified in the same manner as in Example 1. For comparison, measurement of dG and 8OHdG was performed on ultrapure water alone that had been treated in the same manner. The results are shown in Table 7.

TABLE 7

| Test Substance | Concentration | 15 Minutes' standing | 60 Minutes' UV standing |
|---|---|---|---|
| Ultrapure water | | 0.155 | 0.289 |
| $KBrO_3$ | 10 mg/ml | 2.851 | 2.626 |
| | 1 mg/ml | 0.511 | 0.563 |
| | 0.1 mg/ml | 0.159 | 0.131 |

(In the Table above, each measured value is an average of two measured values.)

Potassium bromate is a food additive commonly used as a bleaching agent for bread and antiseptic. From the above results, it can be seen that it exhibits concentration-dependent 8OHdG induction. Since there is no great difference between the standing for 15 minutes and the standing for 60 minutes, the oxidation reaction by potassium bromate is considered to occur quickly and then reach a constant level. The method of the present invention suggests that potassium bromate, which was considered safe according to conventional evaluation tests, could be toxic. AS stated above, permissible concentrations of various food additives taken daily by oral route can be reviewed according to the present invention.

EXAMPLE 8

170 µl portions of a 1 mM sodium ethylenediaminetetraacetate (EDTA) solution, 10% glycerol (Gly) solution, a 1% or 2.5% methanol (Meth) solution, a mixed solution of 10% Gly and 2.5% Meth, a mixed solution of 10% Gly, 2.5% Meth and 1 mM EDTA were injected into each well of a 99-well plastic plate. Then, 10 µl of 400 µg/ml dG (dissolved in ultrapure water) and 20 µl of 50 mg/ml potassium bromate ($KBrO_3$) solution were added to each well and the plate was left to stand as it was at room temperature for 30 minutes. Then, the solution in each well was mixed with the same amount of 20% glycerol solution and dG and 8OHdG were quantified in the same manner as in Example 1. For comparison, measurement of dG and 8OHdG was performed on ultrapure water alone that had been treated in the same manner. The results are shown in Table 8.

TABLE 8

| Test Substance | 30 Minutes' standing |
|---|---|
| Ultrapure water | 2.699 |
| 1 mM EDTA | 0.784 |
| 10% Gly | 1.123 |
| 1% Meth | 2.059 |
| 2.5% Meth | 1.685 |
| 10% Gly + 2.5% Meth | 0.954 |
| 10% Gly + 2.5% Meth + 1 mM EDTA | 0.699 |

(In the Table above, each measured value is an average of two measured values.)

In the presence of potassium bromate acting as an active oxygen generator, the mixed solution f 10% Gly, 2.5% Meth and 1 mM EDTA exhibited the highest antioxidant ability. Based on this, it can be seen that a solution containing these three kinds of components is effective as an antioxidant preservative solution for various test solutions and test samples.

EXAMPLE 9

170 µl portions of ultrapure water and predetermined concentrations of vitamin C (VC), vitamin E (VE), and glucose (Glu) as test substance were added to each well of two 99-well plastic plates and, as additional solution, 20 µl of ultrapure water or predetermined concentration of bisphenol A (BPA) were injected into each well. Then, 10 µl of 400 µg/ml dG (dissolved in ultrapure water) was added to each well. One of the plates was left to stand as it was at room temperature for 90 minutes and the other plate was irradiated with UV light (254 nm, 860 µW/cm$^2$) for 90 minutes in a UV light irradiation box. After completion of the standing or irradiation, the solution in each well was mixed with the same amount of 20% glycerol solution and dG and 8OHdG were quantified in the same manner as in Example 1. The results are shown in Table 9.

TABLE 9

| Test Substance (Concentration) | Additional solution (Concentration) | 90 Minutes' standing | 90 Minutes' UV irradiation |
|---|---|---|---|
| Ultrapure water | Ultrapure water | 0.21 | 0.64 |
| | BPA (50 ppm) | 0.22 | 11.58 |
| | BPA (5 ppm) | 0.31 | 6.19 |
| | BPA (0.5 ppm) | 0.19 | 2.09 |
| VC (0.001%) | Ultrapure water | 16.3 | 5.75 |
| VC (0.001%) | BPA (50 ppm) | 1.51 | 12.53 |
| VC (0.0001%) | BPA (50 ppm) | nd | 15.95 |
| VC (0.00001%) | BPA (50 ppm) | nd | 14.96 |
| VE (0.001%) | Ultrapure water | 0.18 | 0.28 |
| VE (0.001%) | BPA (50 ppm) | 0.29 | 3.79 |
| VE (0.0001%) | BPA (50 ppm) | nd | 8.27 |

TABLE 9-continued

| Test Substance (Concentration) | Additional solution (Concentration) | 90 Minutes' standing | 90 Minutes' UV irradiation |
|---|---|---|---|
| VE (0.00001%) | BPA (50 ppm) | nd | 15.43 |
| Glu (1 mg/ml) | Ultrapure water | 0.16 | 0.40 |
| Glu (1 mg/ml) | BPA (50 ppm) | 0.24 | 4.46 |
| Glu (0.1 mg/ml) | BPA (50 ppm) | nd | 7.52 |
| Glu (0.01 mg/ml) | BPA (50 ppm) | nd | 14.93 |

(In the Table above, each measured value is an average of two measured values, "nd" means no measurement.)

From the above results, the following conclusion can be obtained.

By addition of BPA, 8OHdG upon irradiation with UV light increases depending on concentration.

VE and Glu significantly inhibit the increase in 8OHdG at the time of addition of BPA and irradiation with UV light.

0.001% VC alone potently induces 8OHdG but the effect is cancelled by coexisting of BPA. However, when irradiated with UV light, VC does not cancel the induction of 8OHdG by BPA.

As stated above, gene oxidation ability of BPA undergoes various influences by coexistent substances.

Therefore, use of the measurement method of the present invention enables not only identifying a substance that induces oxidation injury of a gene but also identifying antioxidant substance that is specific to the substance concerned and can cancel its oxidative toxicity and further quantitatively evaluating the antioxidant ability thereof.

EXAMPLE 10

Various kinds of drinking water as test substances (test solutions) were measured of their antioxidant ability or oxidant ability.

dG was dissolved in various kinds of drinking water such that their concentrations were 10 µl/ml. 200 µl of each of the obtained solutions was injected into two test vessels (surface area of the solution was 36 mm$^2$). One of the vessels was left to stand at room temperature for 90 minutes and the other was irradiated with UV light (254 nm, 860 µW/cm$^2$) for 90 minutes in a UV light irradiation box. After completion of the standing or irradiation, the solution in each vessel was mixed with the same amount of 20% glycerol solution and dG and 8OHdG were quantified in the same manner as in Example 1.

The kinds of drinking water tested are as follows.

Ultrapure water: Water having a specific resistance of 18 MegΩ (manufactured by Millipore Systems), having a redox potential of 360 mV.

City water: Ordinary city water in Kasuga City, Fukuokoka Prefecture (collected in July, 1997), having a redox potential of 727 mV.

Processed water: Purified water obtained by passing the above city water through a commercially available water purifier (that purifies water by passing it through activated carbon, a strong magnet, ceramics, etc.), having a redox potential of 518 mV.

Natural water: Groundwater collected at Nichiden City in Ooita Prefecture (water isolated from contamination on the ground surface such as acid rain and fertilizer, dissolved nitrogen oxides concentration is 0.01 ppm or less), having a redox potential of 280 mV.

The results obtained are shown in Table 10.

TABLE 10

| Test Solution | UV light[1] | produced 8OHdG[2] | A ratio of ultrapure water[3] |
|---|---|---|---|
| Ultrapure water | (−) | 0.131 | 1.00 |
|  | (+) | 1.049 | 1.00 |
| City water | (−) | 0.342 | 2.61 |
|  | (+) | 12.561 | 11.97 |
| Processed water | (−) | 0.157 | 1.20 |
|  | (+) | 0.584 | 0.56 |
| Natural water | (−) | 0.091 | 0.69 |
|  | (+) | 0.516 | 0.49 |

[1](+) indicates the case where irradiation with UV light was performed and (−) indicates the case where no irradiation with UV light was performed but left to stand at room temperature for 90 minutes.
[2]Each measured value is an average of measured values of two measurements.
[3]A ratio of each numeral value assuming the value of produced 8OHdG with ultrapure water as 1 is shown.

From the above results, the following conclusion can be obtained.

The oxidizing power that city water has is judged to be very rational in view of sterilization and an antibacterial property.

The water processed through a water purifier (processed water) markedly inhibited induction of 8OHdG and the induction of 8OHdG when irradiated with UV light is performed is at a low value as compared with the case of standing at room temperature.

Natural water significantly inhibits the induction of 8OHdG in both cases of standing at room temperature and irradiation with UV light.

As stated above, according to the present invention, the reducing ability (antioxidant ability) or oxidizing ability of water can be quantified. Using this, correlation between drinking water and various diseases (severity, progress of disease, therapeutic effect, preventive effect, etc.) can be studied. In addition, gene injury induction effect of an aqueous solution containing an unknown substance can be comprehensively evaluated.

EXAMPLE 11

Progressive urine collected from a healthy person was mixed with an antioxidant preservative solution comprising the mixed solution containing 10% Gly, 2.5% Meth and 1 mM EDTA described in Example 8 in a volume ratio of 1:1 and quickly stored by refrigeration (about −20° C.). Immediately before tests, the stored mixed solution concerned was thawed and perfused (1 µl/minute) through micro dialysis treatment using a dialysis membrane having a function of cutting off a molecular weight of 50 kD. Low molecular weight DNA-related components (recovery being about 30 to 40%) extracted by this treatment were subjected to quantification of dG and 8OHdG in the same manner as in Example 1. In addition to the quantification, nitrate ion ($No_3^-$) contained in the same test sample was quantified by use of a high sensitivity nitrogen oxides detector (ENO-10, manufactured by Eicom Corporation).

Figure 2:
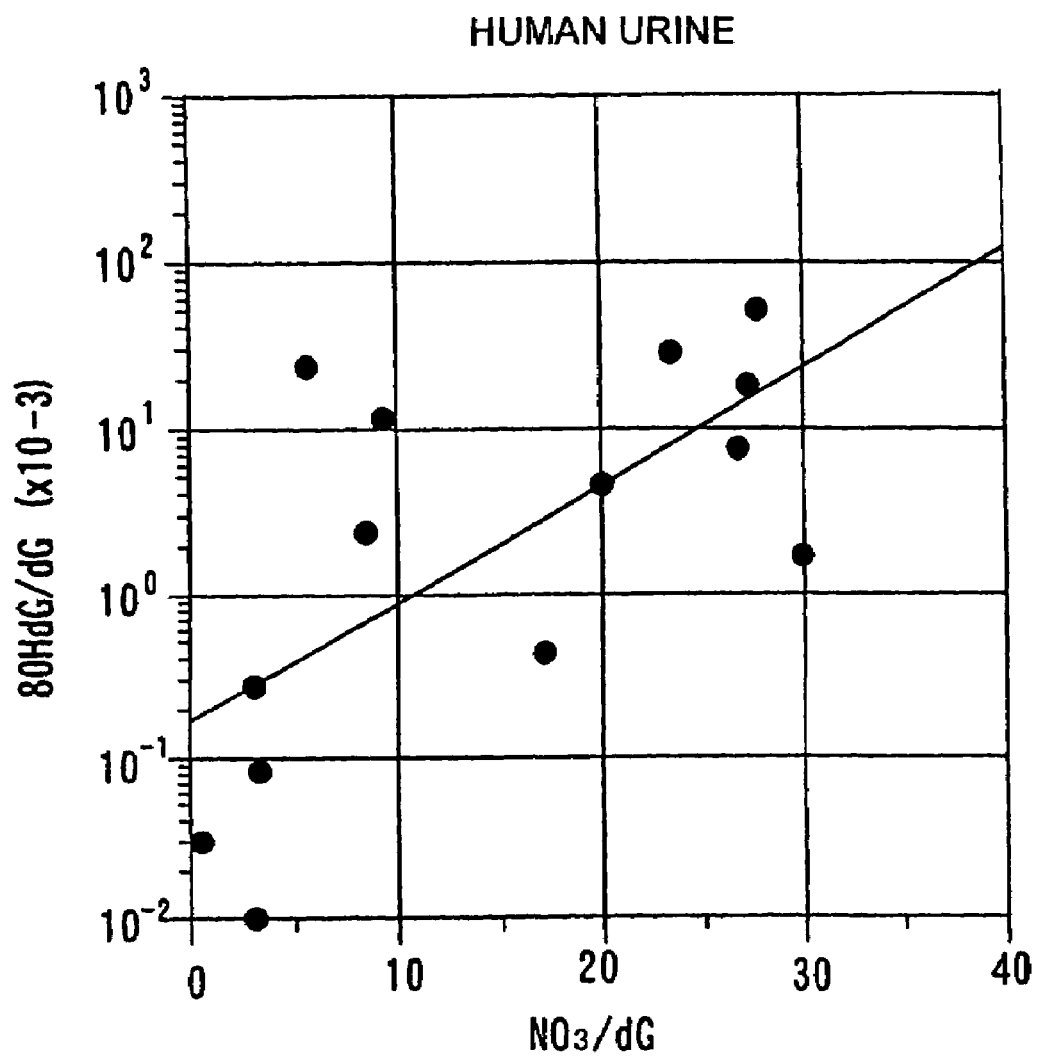
FIG. 2 is a graph illustrating a relationship between a concentration ratio of $NO_3^-/dG$ and that of 8OHdG/dG in human urine measured by use of the biological sample measurement apparatus of the present invention.

The results obtained are shown in the graph in FIG. 2. The X axis in the graph indicates the ratio ($NO_3^-/dG$) of the detected $NO^{3-}$ concentration (µmol/l) and dG concentration (ng/ml) and the Y axis indicates logarithm of the ratio (8OHdG/dG) of the detected 8OHdG concentration (pg/ml) and dG concentration (ng/ml). Also, since the concentration of dG in urine correlates to the concentration ratio of urine, errors in data attributable to difference in the concentration ratio of urine could be excluded by dividing the respective concentration values of $NO_3^-$ and 8OHdG by the concentration value of dG. Further, by expressing the risk of oxidation injury of gene (Y axis) in terms of oxide type (8OHdG)/reduced type (dG), a more rational index can be obtained. For reference, Table 11 shows approximate concentrations of 8OHdG and dG in biological substances detected by the same measurement apparatus as described above.

TABLE 11

| Biological sample | 8OHdG concentration | dG concentration |
|---|---|---|
| Human urine | 10-5000 pg/ml | 50-2000 ng/ml |
| Human plasma | 1-50 pg/ml | 5-25 ng/ml |
| Human cerobrospinal fluid | 2-15 pg/ml | 50-200 ng/ml |
| Mouse brain tissue | 20-50 pg/g | 200-1000 ng/g |
| Mouse testis tissue | 50-100 pg/g | 2000-5000 ng/g |

From the results shown in FIG. 2, it is apparent that the logarithm of 8OHdG/dG and $NO_3^-$/dG ratio are positively correlated ($p<0.05$). This means that the logarithm of 8OHdG/dG is in a positive correlation with the concentration of nitrate ion, a typical oxide in produced in vivo, and that the logarithm of 8OHdG/dG can be an index for in vivo oxidation stress.

Although data are not shown, the studies thus far shows the followings.

In patients with progressive cancers and congenital gene aberration, the value of 8OHdG/dG is shifted upwards from the approximation line plotted on healthy person (i.e., 8OHdG/dG ratio that presumably more strongly reflects oxidation injury of gene shows a relatively higher value than oxidation index on whole individual expressed by $NO_3^-$/dG ratio).

In persons who smoke, there is the tendency that both 8OHdG/dG ratio and $NO_3^-$/dG ratio show high values.

Even in the same individual, when in extraordinary conditions (for example, hangover, cold, after excessive exercise, etc.), the values of 8OHdG/dG and $NO_3^-$/dG ratio are shifted increasing in the upper right direction.

From the above results, the following conclusion can be obtained.

8OHdG/dG value can be an important index of in vivo oxidation.

The value of 8OHdG/dG varies depending on the daily living (eating, exercises, rest, etc.) or the like of a subject and can be an index for stress in a broad sense as including psychosocial factors.

By quantifying influences of natural and artificial chemicals and foods periodically taken by living organism on these indices, harmfulness (carcinogenicity, teratogenicity, reproduction toxicity, etc.) or usefulness (therapeutic or preventive effects for various diseases caused by in vivo oxidation or oxidation injury of gene nucleic acid, refreshing effect, aging preventing effect, etc.) of the natural and artificial chemicals and foods can be rationally evaluated.

Measurement limit of 8OHdG is 0.5 pg/ml (sample amount 50 μl), which is much superior to the measurement limit of 1 ng/ml for the conventional EIA method. Also, measurement limit of dG is 0.2 ng/ml (sample amount 50 μl).

EXAMPLE 12

The following three experiments were conducted on city water, alkali ion water and deep sea salt mineral water and their usefulness was evaluated.

Experiment 1 Quantification of Nitrogen Oxides

In order to measure the contents of nitric acid-form nitrogen and of nitrous acid-form nitrogen, the nitrogen oxides in the above three samples were quantified. High nitrogen oxides content indicates strong contamination with exuded fertilizer components, excrements, sewage, etc. in past and is prescribed to be 10 ppm or less in the water quality standard. Also, it is known that when infants (6 months old or less) take up water containing nitrogen oxides in high concentrations, they suffer methemoglobinemia and their respiratory action is inhibited.

Measurement was conducted by use of a high sensitivity nitrogen oxides analyzer (manufactured by Eicom Corporation, ENO-10) that detects $NO_3$ and $NO_2$ simultaneously from a minute amount of sample, and after separating $NO_3$ and $NO_2$ from each other by use of a reducing column, color developed by diazo coupling reaction was detected by absorbance at 540 nm.

The results obtained are shown in the following table.

| | $NO_2^-$ | | $NO_3^-$ | |
|---|---|---|---|---|
| | Area (mVs) | Concentration (ppm) | Area (mVs) | Concentration (ppm) |
| City water | 1.55 | 0.0016 | 3097.88 | 7.4009 |
| Alkali ion water | 3.46 | 0.0036 | 2525.77 | 6.0341 |
| Deep sea salt mineral water | 4.87 | 0.0050 | 3265.38 | 7.8011 |

As a result of experiments, each sample was in the range of the water quality standard for city water.

Experiment 2 Measurement of Redox Potential

Measurement of redox potential was conducted on the above three samples. Also, for control, experiment was also conducted on ultrapure water.

The results obtained are shown in the following table.

| | ORP (mV) |
|---|---|
| Ultrapure water | 274.6 |
| City water | 695.2 |
| Alkali ion water | −112.4 |
| Deep sea salt mineral water | 120.5 |

Antioxidant ability was high in the order of alkali ion water>deep sea salt mineral water>city water.

Experiment 3 Experiment of Induction of Gene Oxidation Injury

The ability of inducing oxidation injury of gene was measured on the above three samples. In the measurement, samples were added to glass tubes containing a solution of dG in a known concentration and UV light was irradiated for a predetermined time (0 (=immediately after), 0.5, 1 and 2 hours) to oxidize dG. Thereafter, the reaction was terminated with a reaction terminating solution and dG and its oxide, 8OHdG, were separated by high performance liquid chromatography to quantify dG and 8OHdG in the same manner as in Example 1. Also, for control, experiment was also conducted on ultrapure water.

The results obtained are shown in the following tables.

| Time (hr) | 8OHdG (mVs) | dG (mVs) | 8OHdG/dG × $10^4$ |
|---|---|---|---|
| Ultrapure water | | | |
| 0 | 0.2534 | 1113.75 | 2.28 |
| 0.5 | 0.4563 | 1151.98 | 3.96 |
| 1 | 2.2136 | 1157.67 | 19.12 |
| 2 | 5.5788 | 1203.49 | 46.36 |
| City water | | | |
| 0 | 1.8889 | 1101.03 | 17.16 |
| 0.5 | 3.8958 | 1127.45 | 34.55 |
| 1 | 3.8858 | 1145.67 | 33.92 |
| 2 | 2.0812 | 1201.46 | 17.32 |
| Alkali ion water | | | |
| 0 | 0.1051 | 1107.94 | 0.95 |
| 0.5 | 0.7522 | 1114.67 | 6.75 |
| 1 | 0.9715 | 1120.04 | 8.67 |
| 2 | 1.5257 | 1161.09 | 13.14 |
| Deep sea salt mineral water | | | |
| 0 | 0.1302 | 1078.80 | 1.21 |
| 0.5 | 0.5631 | 1117.39 | 5.04 |
| 1 | 0.5103 | 1125.07 | 4.54 |
| 2 | 0.9984 | 1157.90 | 8.62 |

From the results, the following conclusion can be obtained. A higher 8OHdG/dG ration means a stronger effect of gene oxidation injury.

City water exhibits the most potent effect of gene oxidation injury in the case of 0.5 hour, and thereafter it shows a tendency of a decrease.

As compared with ultrapure water, alkali ion water and deep see salt mineral water both exhibit low effect of gene oxidation injury.

Comparing the power of inhibiting the effect of oxidation injury (antioxidant power), the order is deep see salt mineral water>alkali ion water.

As described above, in biological evaluation method of the present invention, the usefulness of city water, alkali ion water, deep see salt mineral water, etc. whose composition cannot be determined exactly can also be evaluated.

EXAMPLE 13

Three experiments were conducted on the following samples in the same manner as in Example 12 and their toxicity was evaluated.

Sample A: Shochu waste liquor stock solution

Sample B: electrolytically treated water obtained from Sample A

Experiment 1 Quantification of Nitrogen Oxides

In the same manner as in Example 12, the nitrogen oxides in Samples A and B were quantified.

The results obtained are shown below.

| | Area (mVs) | | Concentration (ppm) | |
|---|---|---|---|---|
| | $NO_2^-$ | $NO_3^-$ | $NO_2^-$ | $NO_3^-$ |
| Sample A diluted 10 folds | 0.80 | 614.32 | 0.0008 | 0.98 |
| Sample B diluted 10 folds | 31.78 | 13575.81 | 0.0319 | 21.60 |

Sample A $NO_2^-$ 0.008 ppm + $NO_3^-$ 9.8 ppm = $NO_x$ 9.808 ppm
Sample B $NO_2^-$ 0.319 ppm + $NO_3^-$ 216.0 ppm = $NO_x$ 216.319 ppm The above results indicate the followings.

While the upper limit of the concentration of nitrogen oxides is defined to be 10 ppm as a standard by City Water Law, Sample A contained nitrogen oxides in an amount near the upper limit of the standard (9.8 ppm).

Sample B contained nitrogen oxides 20 times or more the upper limit prescribed by the City Water Law (216.3 ppm).

Experiment 2 Measurement of Redox Potential

For Sample A, Stock solution per se was used, and for Sample B, a solution diluted to 10 ppm in terms of the concentration of $NO_3^-$ was used for measurement of redox potential (silver/silver chloride electrode).

As a result of the measurement, the redox potential of Sample A was 184.8 mV while that of Sample B was 715.4 mV.

Experiment 3 Experiment on Gene Oxidation Injury

90 μl of each sample was added to 10 μl of dG solution (200 μg/ml) and stirred for 5 minutes. Thereafter, 100 μl of a reaction terminating solution was added and dG and 8OHdG were simultaneously measured in the same manner as in Example 1.

The results obtained are shown below.

| | dG 200 μg/mL | | 8OHdG/ dG × $10^5$ |
|---|---|---|---|
| | dG (mVs) | 8OHdG (mVs) | |
| Ultrapure water | 1128.40 | 0.0163 | 1.445 |
| Sample A diluted 100 folds | 1104.00 | 0.0015 | 0.136 |
| Sample A diluted 1000 folds | 1098.00 | 0.0085 | 0.774 |
| Sample B diluted 100 folds | 109.52 | 2.7460 | 2507.300 |
| Sample B diluted 1000 folds | 971.34 | 5.8810 | 605.450 |

From the above results, the followings can be deduced.

The ability of Sample A to induce gene oxidation injury is not so high, which evidences that microbes can propagate in Sample A.

Sample B has a toxicity strong enough to destruct dG itself and when diluted 1,000 folds, its toxicity cannot be neutralized.

As stated above, in the biological evaluation method of the present invention, shochu waste liquor and shochu waste liquor after electrolytic treatment can be evaluated for their toxicity.

EXAMPLE 14

Treatment was conducted by adding a catalyst as indicated below to Sample B of Example 13 to examine the content of nitrogen oxide and a change in the ability of inducing gene oxidation injury.

Treating Conditions:
(1) Sample B+Magnetic iron ore (2 g)+$TiO_2$ (0.5 mg)
(2) Sample B+Magnetic iron ore (2 g)+C (0.5 mg)
(3) Sample B+Magnetic iron ore (2 g)+$TiO_2$ (0.5 mg)+C (0.5 mg)
(4) Sample B+Magnetic iron ore (2 g)+$TiO_2$ (0.5 mg)+magnet
(5) Sample B+Magnetic iron ore (2 g)+C (0.5 mg)+magnet
(6) Sample B+Magnetic iron ore (2 g)+$TiO_2$ (0.5 mg)+C (0.5 mg)+magnet
(7) Sample B+Magnetic iron ore (2 g)+$TiO_2$ (0.5 mg)+magnet+US (42 KHz, 300 W)
(8) Sample B+Magnetic iron ore (2 g)+C (0.5 mg)+magnet+US (42 KHz, 300 W)
(9) Sample B+Magnetic iron ore (2 g)+$TiO_2$ (0.5 mg)+C (0.5 mg)+magnet+US (42 KHz, 300 W)
*$TiO_2$: Titanium dioxide, C: activated carbon, US: Ultrasonic wave In each of brown bottles containing respective catalysts described above, 30 ml of Sample B was added and left to stand at room temperature for 15 minutes. Thereafter, if ultrasonic wave is to be applied, it was exposed to ultrasonic wave for 30 minutes.

Experiment 1 Quantification of Nitrogen Oxide

The solutions treated as described above were each diluted 20 folds and quantification of nitrogen oxide was performed in the same manner as in Example 12.

The results obtained are shown below.

| | Magnetic iron ore | $TiO_2$ | C | Magnet | US | $NO_3$ area (mVs) | Concentration of $NO_3$ (ppm) |
|---|---|---|---|---|---|---|---|
| Sample B | | | | | | 4338 | 189 |
| Treatment (1) | + | + | | | | 4217 | 183 |
| Treatment (2) | + | | + | | | 4128 | 179 |
| Treatment (3) | + | + | + | | | 4003 | 174 |
| Treatment (4) | + | + | | + | | 3885 | 169 |
| Treatment (5) | + | | + | + | | 3895 | 169 |
| Treatment (6) | + | + | + | + | | 3670 | 159 |
| Treatment (7) | + | + | | + | + | 3962 | 172 |
| Treatment (8) | + | | + | + | + | 3905 | 170 |
| Treatment (9) | + | + | + | + | + | 4155 | 181 |

From the above results, the following conclusion can be obtained.

The concentration of $NO_3$ decreased as compared with the electrolytically treated solution of Sample B under any one of the treating conditions (1) to (9).

$TiO_2$ and activated carbon gave more improved reduction efficiency in $NO_3$ when used in combination than when used alone.

Addition of a magnet further improved the efficiency of reduction in $NO_3$.

Application of ultrasonic wave rather showed a tendency of an increase in $NO_3$. This is presumed to be attributable to occurrence of various chemical reactions including oxidation reaction by application of ultrasonic wave.

Condition (6) gave the highest efficiency of reduction in $NO_3$, in which $NO_3$ is decreased by about 16% as compared with Sample B (189 ppm→159 ppm).

By studying conditions such as amount of catalyst, the efficiency of reduction in $NO_3$ is supposed to be further increased.

Experiment 2 Gene Oxidation Injury Test

Gene oxidation injury test was conducted on Sample B and a solution obtained by performing treatment (9) to Sample B and a change in the ability of inducing gene oxidation injury was observed.

In the test, 10 μl of dG (200 μg/ml) was added to 90 μl of the sample and the mixture was stirred for 5 minutes. Thereafter, 100 μl of a reaction terminating solution was added thereto and dG and 8OHdG were simultaneously measured in the same manner as in Example 1.

Each of the results obtained in the case of performing the catalyst treatment for 2 days and the case of performing the catalyst treatment for 1 month is shown below.

| | dG 200 μg/mL | |
|---|---|---|
| | dG (mVs) | 8OHdG (mVs) |
| [Catalyst treatment for 2 days] | | |
| Ultrapure water | 1054 | 0.010 |
| Sample B stock solution | 0.29 | nd |
| Sample B diluted 10 folds | nd | 32.820 |
| Sample B diluted 100 folds | 14.28 | nd |
| Sample B diluted 1000 folds | 1008 | 2.045 |
| Sample B diluted 10000 folds | 1108 | nd |
| Catalyst (9) of sample B stock solution | 2.82 | nd |
| Catalyst (9) of sample B | 946 | 0.135 |

-continued

| | dG 200 μg/mL | |
|---|---|---|
| | dG (mVs) | 8OHdG (mVs) |
| diluted 10 folds | | |
| Catalyst (9) of sample B diluted 100 folds | 1135 | 0.060 |
| Catalyst (9) of sample B diluted 1000 folds | 1112 | 0.053 |

-continued

| | dG 200 μg/mL | |
|---|---|---|
| | dG (mVs) | 8OHdG (mVs) |
| [Catalyst treatment for 1 month] | | |
| Ultrapure water | 1101.67 | 1.97 |
| Catalyst (9) of Sample B stock solution | 1040.27 | 4.94 |
| Catalyst (9) of Sample B diluted 10 folds | 1138.57 | 4.09 |
| Catalyst (9) of Sample B diluted 100 folds | 1094.50 | 5.89 |
| Catalyst (9) of sample B diluted 1000 folds | 1087.78 | 2.70 |

The above results indicate the followings.

Sample B has a toxicity strong enough to destruct dG itself and it is necessary to dilute it 10000 folds or more in order to neutralize its toxicity.

The solution obtained by treating Sample B according to the treatment (9) showed a drastic reduction in its toxicity when diluted at least 10 folds. Therefore, it is highly possible that the treatment (9) can detoxicate the biotoxicity of the electrolytically treated water.

By continuing the treatment according to the treatment (9) for 1 month, the toxicity of the solution was drastically decreased.

Therefore, it is understood that the treatment according to the treatment (9) proceeds with time.

As described above, the biological evaluation method of the present invention can provide an assist to determine an optimal treating method by evaluating toxicity of solutions treated by various methods.

EXAMPLE 15

Both quantification of nitrogen oxides and gene oxidation injury test were performed on each of industrial wastewaters subjected to the following treatments and the results of wastewater treatments were examined.

Sample C: Industrial wastewater electrolytically treated on platinum electrode
  COD at completion of the treatment: 350 ppm
  Concentration of hypochlorous acid at completion of the treatment: 3,013 ppm Sample D: Industrial wastewater electrolytically treated on platinum/iridium electrode
  COD at completion of the treatment: 2,600 ppm
  Concentration of hypochlorous acid at completion of the treatment: 1,560 ppm Experiment 1 Quantification of Nitrogen Oxides After diluting Samples C and D at 100 folds, respectively, the nitrogen oxides in Samples A and B were quantified in the same manner as in Example 12.

The results obtained are shown below.

| | Area (mVs) | | Concentration (ppm) | |
|---|---|---|---|---|
| | $NO_2^-$ | $NO_3^-$ | $NO_2^-$ | $NO_3^-$ |
| Sample C diluted 100 folds | 1.99 | 2158.65 | 0.00216 | 2.6269 |
| Sample D diluted 100 folds | 20.65 | 3707.87 | 0.02245 | 4.5122 |

Experiment 2 Gene Oxidation Injury Test

Gene oxidation injury test was conducted on Samples C and D and a change in the ability of inducing gene oxidation injury was observed.

In the test, 10 μl of dG (200 μg/ml) was added to 90 μl of each sample and the mixture was stirred for 5 minutes. Thereafter, 100 μl of a reaction terminating solution was added thereto and dG and 8OHdG were simultaneously measured in the same manner as in Example 1.

The results obtained are shown below.

| | dG 200 μg/mL | | 8OHdG |
|---|---|---|---|
| | dG (mVs) | 8OHdG (mVs) | 100 ng/mL (mVs) |
| Ultrapure water | 1114.2 | 0.16 | 9.72 |
| Sample C stock solution | 0.35 | 0.02 | nd |
| Sample C diluted 10 folds | 0.04 | 0.72 | 4.88 |
| Sample C diluted 100 folds | 687.3 | 2.19 | 0.04 |
| Sample C diluted 1000 folds | 1149.8 | 2.01 | 0.42 |
| Sample C diluted 10000 folds | 1095.7 | 2.88 | 8.81 |
| Sample C diluted 100000 folds | 1116.3 | 3.67 | 8.83 |
| Sample D stock solution | 1085.5 | 4.90 | 9.21 |
| Sample D diluted 10 folds | 1096.1 | 4.36 | 6.70 |
| Sample D diluted 100 folds | 1078.1 | 4.60 | 8.50 |
| Sample D diluted 1000 folds | 1094.5 | 3.72 | 9.42 |
| Sample D diluted 10000 folds | 1081.4 | 3.94 | 9.74 |
| Sample D diluted 100000 folds | 1076.1 | 2.98 | 9.00 |

From the above results, the following conclusion can be obtained.

The stock solution of Sample C has a very strong toxicity. In order to neutralize the toxicity, it is necessary to dilute it 10000 folds or more.

The toxicity of Sample D mostly disappeared. The change of treating conditions would result in a considerable difference from Sample C.

As state above, according to the biological evaluation method of the present invention, the usefulness of treating method used can be evaluated by testing the solution after the treatment.

EXAMPLE 16

To examine the correlation between milk nutrition of infants and 8OHdG excretion amount in urine, tests were conducted in the following procedure.

First, with respect to infants of 1 to 3 months after birth, they were grouped into those who are grown mainly with mother's milk (n=6), grown mainly with powder milk (n=8), and grown with mixed nutrient (n=6). Urines progressively collected from these infants were freeze-preserved and the concentration of 8OHdG therein was measured by use of an 8OHdG enzyme immune antibody (EIA) measuring kit (manufactured by Nippon Oil & Fats Co., Ltd., measurement sensitivity>1 ng/ml). Further, 100 μl of same frozen sample after thawing was added to a preservation tube containing 200

μl of an antioxidant preservative solution comprising 40% of glycerol, 10% of methanol, and 2 mM EDTA to prepare a mixed solution of test urine and the preservative solution. Then, in the mixed solution, a micro dialysis system (50 KD cut off cellulose membrane, membrane length 10 mm, manufactured by Eicom Corporation) was used to flow a perfusion solution (20% glycerol solution) at a rate of 1 μl/minute (37° C.) and the recovered perfusion solution was ice cooled. The recovery (30 to 40%) of the standard solutions of 8OHdG and of dG under the same condition was confirmed for every probe of micro dialysis in advance. 10 μl of the perfusion solution was automatically dispensed into a 8OHdG/dG simultaneous measurement system as used in Example 1 by use of an automatic dispenser (4° C.). The mixed solution was diluted 10 folds with 100% methanol solution and protein component was precipitated by centrifugation. The concentration of nitrate ion in the supernatant liquid thereof was measured by use of a high sensitivity nitrogen oxides measurement apparatus (ENO-10, manufactured by Eicom Corporation).

Figure 3:
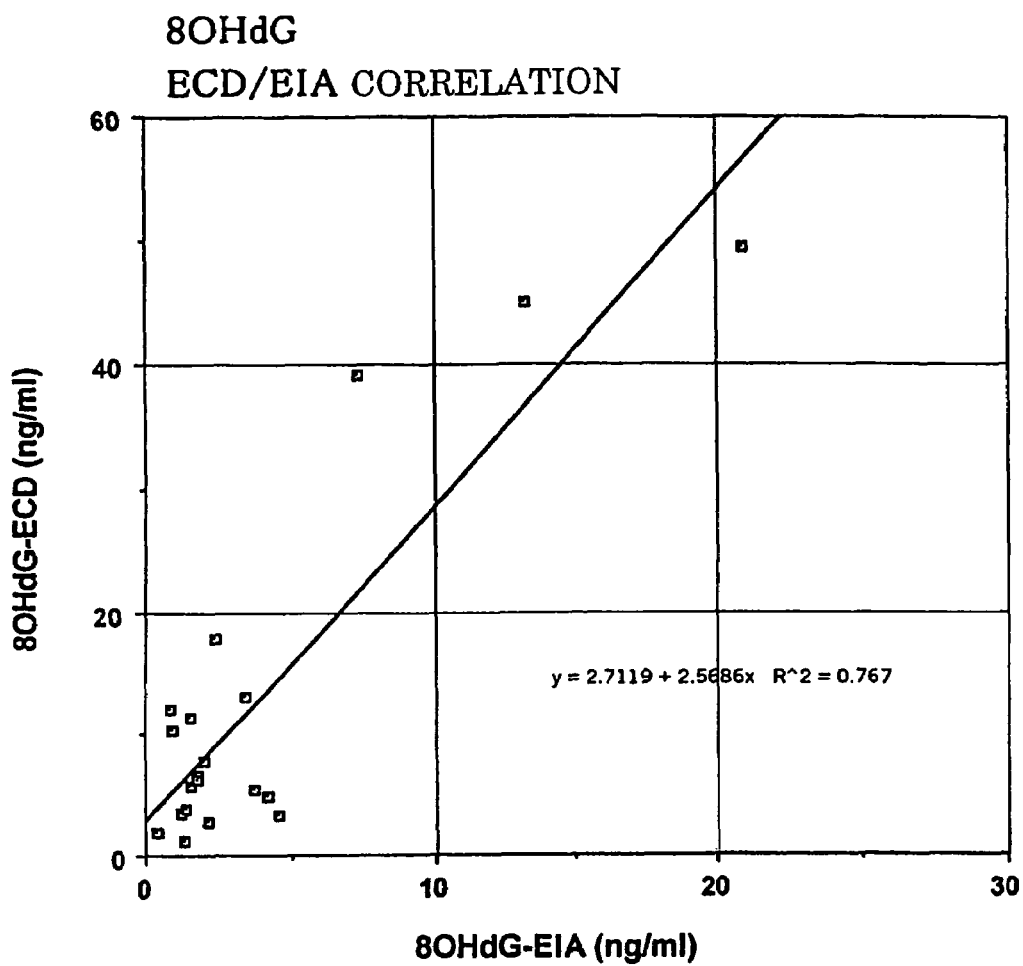
FIG. 3 is a graph illustrating a correlation of 8OHdG concentration obtained by HPLC+electrochemical detector (ECD) method and that obtained by EIA method.
Figure 4:
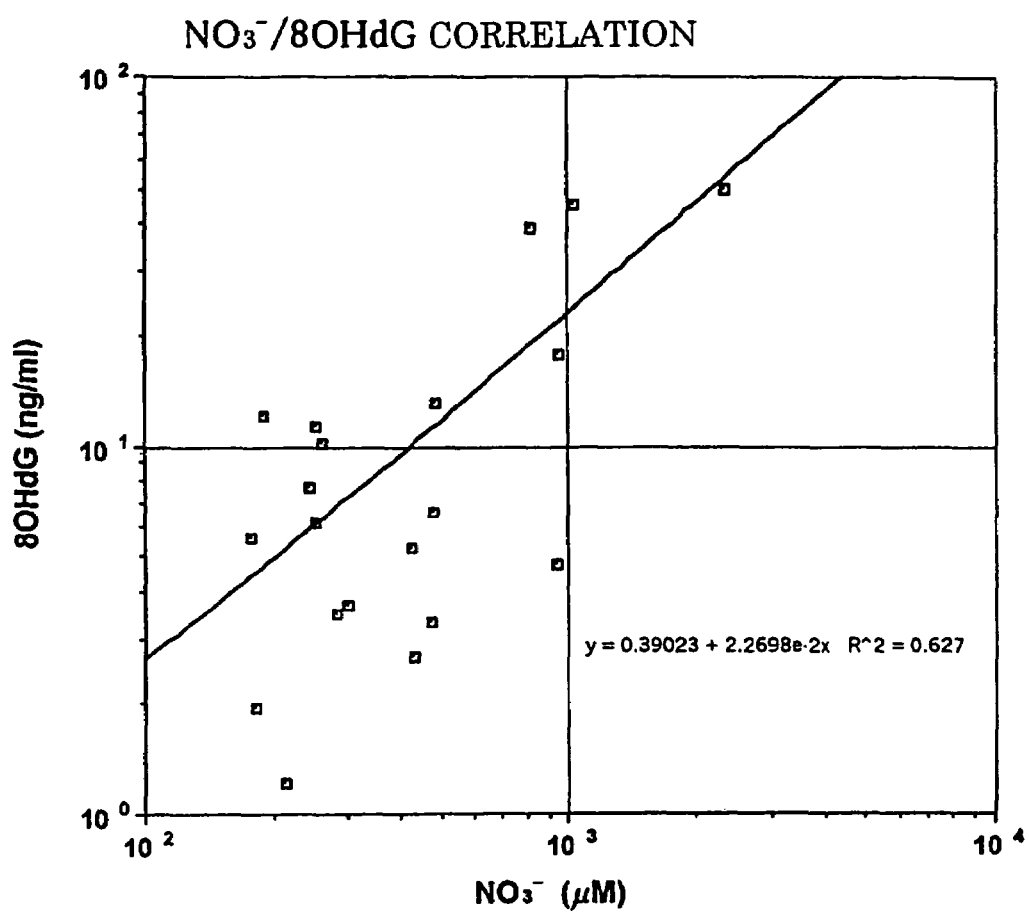
FIG. 4 is a graph illustrating a correlation between 8OHdG concentration and nitrate ion ($NO_3^-$) concentration in urine.
Figure 5:
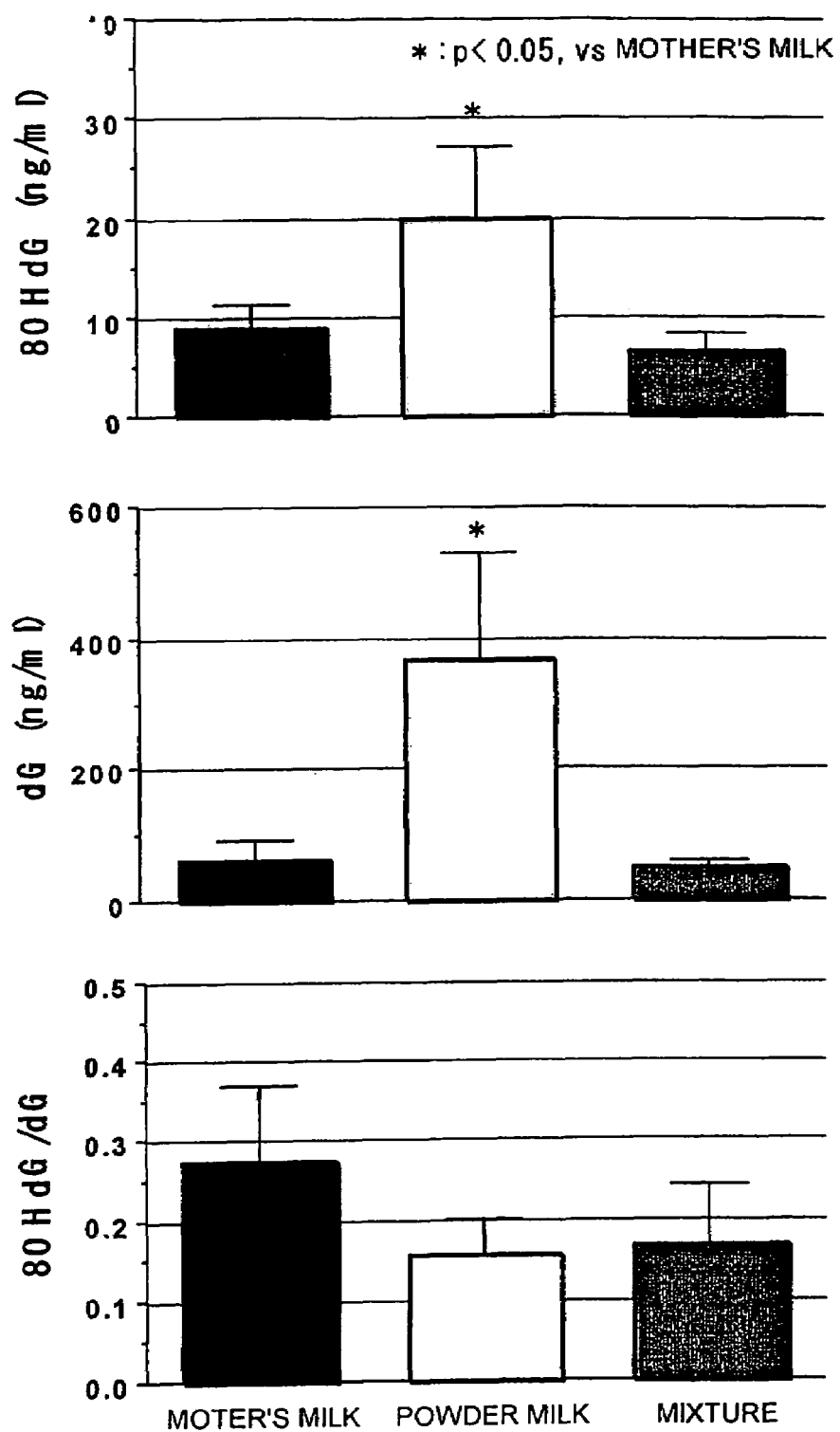
FIG. 5 is bar graphs representing 8OHdG concentration, dG concentration, and a ratio of 8OHdG concentration to dG concentration for each of mainly breast-fed group, mainly powder milk-fed group, and mixed nutrient-fed group.

The results obtained are shown in FIGS. 3 to 5.

FIG. 3 indicates the followings.

A positive correlation with a correlation coefficient of $R^2=0.767$ was observed between the ECD method and the EIA method.

In the results obtained this time, the measurement values by ECD were relatively higher than the measurement values by EIA. Presumably, this is because there was a time lag of several months from collection of analytes to addition of a preservative solution thereto, which time lag have induced spontaneous oxidation of the analytes.

Further, FIG. 4 indicates the followings.

A positive correlation with a correlation coefficient of $R^2=0.627$ was observed between the concentrations of 8OHdG and of $NO^{3-}$.

Generally, the concentration of $NO^{3-}$ in urine is considered as an index for in vivo oxidation stress. Therefore, in consideration of the fact that the positive correlation was observed between the concentrations of 8OHdG and of $NO^{3-}$, it is suggested that the concentration of 8OHdG is also useful as an index for in vivo oxidation stress in general.

Further, FIG. 5 indicates the followings.

The amount of 8OHdG excreted in urine was significantly higher in the powder milk group than in the mother's milk group. However, the excretion amount of dG was also high, so that there was no difference in 8OHdG/dG ratio among the groups.

Recently, reports have been made which focus only on the amount of 8OHdG excreted in urine when evaluating the health of subjects. However, the results obtained this time indicate that total amount of nucleic acid excreted in urine varies greatly according to the composition of nutrient taken up and hence the amount of 8OHdG excreted in urine could not be a rational index for gene oxidation injury unless the amount of excreted dG (generally about 10 times that of 8OHdG) is simultaneously taken into consideration.

In this connection, the measurement apparatus according to the present invention enables one to always perform simultaneous measurement of 8OHdG and dG in the same sample at the same time, so that it has a great advantage over other measurement methods (such as EIA method and LC-MAS method).

INDUSTRIAL APPLICABILITY

As described in detail above, the biological evaluation method for evaluating natural and artificial chemicals by use of a DNA injury indey according to the present invention enables one to evaluate biological toxicity, usefulness, or safety, etc. of test substances such as natural or artificial chemicals or foods in vitro in a very simple manner and at low costs, and thereafter to perform evaluation thereof in vivo, for example cultured cells or in animals depending on importance of the test substances.

It is virtually impossible to conduct conventional full-scale animal experimentation or clinical experimentation for each of artificial chemicals since over 100,000 kinds of these exist even when only principal ones thereof are counted. Therefore, the method of the present invention that can provide a specific DNA injury index in a simple manner for each chemical can provide very useful information in establishing a broad safety standard of concentration or in considering necessity of full-scale animal experimentation or clinical experimentation. Therefore, the biological evaluation method of the present invention provides a means for simply screening biological toxicity of various natural or artificial chemicals or harmfulness/usefulness of foods, and so forth.

The method of the present invention can objectively quantify usefulness and harmfulness of health food or functional food on the market or under currently development. That is, according to the present invention, not only evaluation of usefulness, safety, etc., which must necessarily be conducted for foods currently under development can be reliably and easily performed but also reconfirmation of usefulness and safety of the foods currently on the market can be made.

Further, also the influence of UV light irradiation to a substance (test substance) and the influence of coexisting active oxygen species generator or gene oxidation injury inducing substance on that substance can be simply evaluated according to the present invention, so that the toxicity, etc., of test substance in nature can be more accurately evaluated.

In the method of the present invention, using an aqueous solution containing an unknown substance as a test solution, the gene injury inducing effect of the aqueous solution can comprehensively evaluate; therefore, biological toxicity index for city water, natural water, or the like, whose chemical composition is not clear, can be obtained accurately and easily.

According to the present invention, harmfulness or usefulness of a chemical or food can be accurately and easily evaluated based on the ratio of contents of 8-hydroxy-2'-deoxyguanosine and of 2-deoxyguanosine in products derived from living organism cells, such as urine, blood, etc. collected from animals including humans administered with a chemical or a food.

The high measurement sensitivity and reliability of measurement results by the measurement apparatus of the present invention are most advantageously exhibited when all of the antioxidant preservative solution of a biological sample (in particular nucleic acid component), deproteinization treatment under antioxidative environment (application of a micro dialysis method), and the 8OHdG/dG simultaneous measurement system of the present invention are combined, and a wholly new measurement apparatus capable of measuring DNA oxidation injury index for almost all biological samples can be provided. That is, oxides of nucleic acid that can be detected by an electrochemical detector, for example, 2OHdA that causes conversion of from A:T into G:C in the same manner as 8OHdG and its reduced form, dA, can be simultaneously detected under substantially the same measurement conditions as in the case of 8OHdG/dG.

The micro dialysis treatment used in the measurement apparatus of the present invention is applicable to either of liquid samples and cell-containing samples. Since no acid, alkali or enzyme reaction is used for deproteinization treatment and all the operations can be carried out at low temperatures, analytes are susceptible to less deterioration and since extraction efficiency of DNA related substances depends only on recovery from the dialysis membrane, there is also an advantage such that error can be reduced by using constant perfusion conditions. Further, when the perfusion solution to be used is the same as the preservative solution, a long term storage of analytes after the perfusion is possible.

According to the 8OHdG/dG simultaneous measurement method of the present invention, nucleosides of non-oxidized and of oxidized types can be simultaneously quantified on the same sample, and data processing of the both data as a ratio can exclude or reduce error factors such as dispensing amount of analytes. In addition, cost efficiency in service can be greatly improved because measurement is possible even when the sample injection amount at a time is extremely small at 10 to 100 μl; useful life of the column can be extended since the solution mainly injected into the column is a dialysis membrane perfusion solution and thus measurement noise is small and a higher measurement sensitivity than that attained in the prior art can be expected, and the power saving of the system is possible by connecting to an autoinjector equipped with a constant temperature cooler, since samples to be measured are stable at low temperatures.

The antioxidant preservative solution of the present invention can substantially inhibit oxidation of samples that tend to start oxidizing immediately after their collection during preservation, in contrast to conventional simple freezing or cooling preservation, in which there is the fear that the concentration of oxides in biological may become even higher. Since it is adjusted so as to minimize variation in concentration of, in particular, nucleoside derived from nucleic acid, and oxides thereof, it is most suitable for the preservation of analytes whose DNA oxidation injury indices are to be measured. Further, the antioxidant preservative solution is of relatively simple composition and hence it is inexpensive and the included components are stable, so that it can be preserved for long time.

The invention claimed is:

1. A biological evaluation method of a natural or artificial chemical, comprising the steps of adding a known amount of 2'-deoxyguanosine to a solution containing a specific natural or artificial chemical and an antioxidative preservative solution comprising 0.5 to 2 mM/L of EDTA, 2 to 5 wt % of methanol and 10 to 40 wt % of glycerol, applying UV light to said solution, quantifying 8-hydroxy-2'-deoxyguanosine (8OHdG) and 2'-deoxyguanosine (dG) in said solution; and evaluating harmfulness or usefulness of said natural or artificial chemical based on a ratio (8OHdG/dG) of an amount of 8OHdG to an amount of dG.

2. A biological evaluation method of a natural or artificial chemical, comprising the steps of adding a known amount of 2'-deoxyguanosine to a solution containing a specific natural or artificial chemical and an antioxidative preservative solution comprising 0.5 to 2 mM/L of EDTA, 2 to 5 wt % of methanol and 10 to 40 wt % of glycerol, adding potassium bromate to said solution, quantifying 8-hydroxy-2'-deoxyguanosine (8OHdG) and 2'-deoxyguanosine (dG) in said solution; and evaluating harmfulness or usefulness of said natural or artificial chemical based on a ratio (8OHdG/dG) of an amount of 8OHdG to an amount of dG.

* * * * *